(12) United States Patent
Shire et al.

(10) Patent No.: US 11,497,913 B1
(45) Date of Patent: Nov. 15, 2022

(54) MICRO-FABRICATED ELECTRODE ARRAYS WITH FLEXIBLE SUBSTRATE FOR HIGHLY CHARGE-EFFICIENT AND SELECTIVE STIMULATION OF NERVE TISSUE

(71) Applicant: Bionic Eye Technologies, Inc., Ithaca, NY (US)

(72) Inventors: Douglas Bourne Shire, Ithaca, NY (US); Marcus Gingerich, Ithaca, NY (US); William Drohan, Bedford, MA (US)

(73) Assignee: Bionic Eye Technologies, Inc., Ithaca, NY (US)

( * ) Notice: Subject to any disclaimer, the term of this patent is extended or adjusted under 35 U.S.C. 154(b) by 257 days.

(21) Appl. No.: 16/289,519

(22) Filed: Feb. 28, 2019

Related U.S. Application Data

(60) Provisional application No. 62/636,180, filed on Feb. 28, 2018.

(51) Int. Cl.
| | | |
|---|---|---|
| *A61N 1/05* | (2006.01) | |
| *A61N 1/36* | (2006.01) | |
| *H05K 1/02* | (2006.01) | |
| *H05K 1/09* | (2006.01) | |
| *H05K 1/03* | (2006.01) | |

(52) U.S. Cl.
CPC ....... *A61N 1/36125* (2013.01); *H05K 1/0277* (2013.01); *H05K 1/0353* (2013.01); *H05K 1/09* (2013.01); *A61N 1/0543* (2013.01); *H05K 2201/0326* (2013.01); *H05K 2201/0338* (2013.01)

(58) Field of Classification Search
CPC .............. A61N 1/0551; A61N 1/36071; A61N 1/36062; A61N 1/36185; A61N 1/0553
See application file for complete search history.

(56) References Cited

U.S. PATENT DOCUMENTS

| | | | | |
|---|---|---|---|---|
| 2014/0249612 A1* | 9/2014 | Bonmassar | ........ | C09K 19/3809 607/116 |
| 2018/0200505 A1* | 7/2018 | McLaughlin | ...... | A61N 1/36071 |

* cited by examiner

*Primary Examiner* — Jon Eric C Morales
(74) *Attorney, Agent, or Firm* — Aleksandar Nikolic

(57) ABSTRACT

A method and apparatus of electrode interfaces for stimulating neurons and nerve cells that provides micro-fabricated electrode interfaces configured for conformal placement adjacent to neuron, nerves and neural tissue to thereby allow the neuron, nerves and neural tissue to grow around the electrode interfaces and allow for the creation depending on configuration of local or far electrical fields and current flows to stimulate them.

20 Claims, 8 Drawing Sheets

MICRO-FABRICATED ELECTRODE ARRAYS WITH FLEXIBLE SUBSTRATE FOR HIGHLY CHARGE-EFFICIENT AND SELECTIVE STIMULATION OF NERVE TISSUE

CROSS-REFERENCE TO RELATED APPLICATIONS

This application claims the benefit of priority under US Law and Applicable Foreign law and Treaties of U.S. Provisional Application Ser. No. 62/636,180 filed on Feb. 28, 2018 the content of which is relied upon and incorporated herein by reference in its entirety.

TECHNICAL FIELD

The disclosure relates generally to a process and apparatus for implantable prosthetic devices and system implantable in living tissue and more particularly to a process and apparatus for neural tissue for the restoration of function.

BACKGROUND

Neural prosthetic devices offer the opportunity to restore lost neurological function by delivering electrical (or other forms of) stimuli to nerve cells. The success of cochlear implants is one of the best examples of how a neurological function (e.g. hearing) can be restored by controlled and strategic delivery of electrical stimuli, in this case to the auditory nerve. Partly motivated by this type of success, various research groups and companies have developed or at least conceived of ideas of restoring other types of neurological function, like vision or motor control for Parkinson's disease, by implanting a neural prosthetic device.

In many respects, the success of the cochlear implants was driven by technological improvements, especially engineering advances related to sound processing and electrical stimulation methods. Remarkable success has been achieved for members of the deaf population with cochlear implants that have as few as four electrodes. Attempts to translate this type of success into other systems, particularly the visual system, have not been as successful, partly because more complex neurological functions (like vision) will certainly require more advanced stimulation strategies and a much larger numbers of electrodes to create spatially-detailed visual images.

As such, a general goal for any neural prosthetic device that is designed to restore a complex neurological function is to deliver finely-tuned stimuli to a selected population of nerve cells, without damaging the cells that are the intended sites of stimulation. It is well-known that the electrical stimulation can damage or destroy the delicate neurons, and as a consequence for instance, all groups that have tested retinal prosthetic devices have used relatively large, planar stimulating electrodes. These electrodes spread the stimulating electrical charge over a wider area and thus lower the electrical charge density (vs. that which would be delivered through a smaller electrode for an equal stimulus charge). Lower charge density is generally held to be one important feature for lowering the risk of electrical stimulation damage.

The use of larger electrodes, however, has a negative consequence—it becomes more difficult to selectively stimulate a smaller number of neurons or a selective population of neurons. The reduced specificity of stimulation would make it harder to provide specific neurological functions that require carefully orchestrated coordination among nerve cells to create a particular type of experience, like the ability to see. Hence, larger electrodes are safer but they complicate attempts to restore specific types of neurological function.

One strategy to achieve safer stimulation while also achieving higher specificity of activation of nerve cells is to use an electrode array that allows the target neural tissue to mold around the electrode sites. The closer proximity of the stimulating electrodes to the nerve cells that results reduces the amount of electrical charge needed to activate the nerve cells, and the smaller electrical charge also reduces the number of nearby neurons that are stimulated (which thus improves the specificity of neuronal stimulation). This logic has been applied to the development of several types of electrode arrays which have used rigid structures (i.e., "tines") or even very small diameter wires to enter nerve tissue and achieve proximity to neurons. In some embodiments, a tine might contain more than one stimulating electrode site. Generally, forceful penetration of neural tissue results in a scarring or gliotic response, which can increase the electrical impedance of the tissue surrounding the tines and thereby require higher voltages and/or current densities for stimulation to achieve the same desired responses.

Traditional methods for making these types of penetrating electrode arrays have had significant limitations, at least when considering more advanced applications of neural prosthetic devices to restore more intricate neurological functions than have been attempted to date. For instance, use of traditional (i.e. non micro-fabricated) methods to make electrode arrays has led to the development of arrays made of relatively large wires (≥100 microns in diameter) which are most typically assembled and held together with a polymer, most typically silicone. Arrays with larger diameter wires tend to be relatively stiff, which is undesirable for some applications but desirable for others, like perhaps when delivering the electrode arrays through brain tissue to reach deep nuclei within the brain, as is currently being done to treat some of the movement disorders associated with Parkinson's disease. The potential benefit of added stiffness for these arrays with larger diameter wires comes with the significant disadvantage of reducing the specificity of stimulation. On the other hand, the use of smaller diameter wires makes it possible to fit a larger number of electrodes into a given area of an array, but these arrays tend to be fairly limp, which would not allow them to be inserted deep into the brain. The arrays can be made to be stiffer (by potting them in silicone, for instance), but this approach has a finite limitation in terms of how many hand- or machine-laid wires can be delivered by this type of traditional (i.e. non micro-fabricated) method.

More advanced electrode arrays have been made with micro-fabrication methods, which offer the extraordinary advance of being able to produce arrays with substantially more wires per unit area (i.e. easily a factor of 10-100 more electrodes). The much thinner wire traces (which can be a couple of microns in width, or even nano-scale) can provide for the hundreds or thousands of electrodes that some researchers believe will be needed to create high quality vision with a visual prosthesis. These arrays have been made in one of two forms: 1) a micro-fabricated structure on a rigid substrate with rigid tines; or 2) an ultra-thin and flexible array that has been used to deliver electrical stimulation along a planar surface (like the epi- or sub-retinal surface). The former has been exceptionally useful to reach cortical neurons, which lie just a couple of millimeters below the surface of the cortex, but this approach could not be used to reach deeper neuronal structures, like those that are being stimulated to treat Parkinson's disease. The rigid tines made by micro-fabrication methods are simply too fragile to be passed through a large volume of relatively dense brain tissue. A second type of array form (i.e. an ultra-thin and flexible array) has not heretofore been used for deep brain stimulation, possibly because of the perceived challenges of delivering such a flexible device deep into the brain. We have tested this conceptual advance, which is detailed in the claims of this provisional application.

A review of existing patents and patent applications (through the U.S.P.T.O.) seems to reveal that no person or group has protected the broad concept of using non-rigid, nano-fabricated electrode arrays to stimulate the nervous system.

There have been a number of prior patents granted for retinal prostheses of varying materials, such as a diamond penetrating electrode array (Meffin H, published Jul. 5 2016, #U.S. Pat. No. 9,381,341B2), or those utilizing carbon nanotubes (Gefen, published 6 May 2014, #U.S. Pat. No. 8,718,784B) Our device differs from these in materials, design and manufacturing processes, as detailed further below and in the claims.

A previous patent application (McCreery D B, submitted Dec. 7, 2006; #US20060276866) discusses use of a "silicon-substrate" probe to electrically stimulate deep brain nuclei (claims 1 and 9). Although this description is relevant to our concept, the claims do not speak to the incorporation of the electrode array into a system that could be used to chronically treat a wide range of problems of the nervous system. Further, the technological approach that can be gleaned from the application (i.e., Bosch-process deep reactive ion etching) differs from our approach, which would produce more flexible electrode arrays. (McCreery speaks to the development of a "relatively strong and rigid structure", which differs from our plan to develop a more flexible system.)

Our approach differs from the work of three other main companies in this field, NanoRetina, IMI and Pixium (IP from Stanford University), which use photosensor arrays in their devices. In comparison, our electrodes are not photosensitive, and require external electrical input.

ie. NanoRetina=Gefen, published 21 Jun. 2016, #US937041782; Gefen, published 6 May 2014, #U.S. Pat. No. 87,187,848; Gross, published 23 Feb. 2016, #U.S. Pat. No. 9,265,945B2; Liran, published 24 Nov. 2015, #U.S. Pat. No. 9,192,464B2; Gefen, published 14 Feb. 2017, #U.S. Pat. No. 9,566,191B2)

IMI=Chow, published 6 Nov. 2012, #U.S. Pat. No. 8,306,626B2

Stanford/Pixium=Palanker, published 28 Jul. 2005, #WO2004073547A3

Use of micro-fabrication technology has been promoted for many years as a methodology applicable for neural stimulation by Kensall D. Wise, Ph.D. (University of Michigan). Also, U.S.P.T.O. application #2007/0197892 (Jessie Y. Shen) speaks to the use of micro-fabrication technology to create neural stimulating devices. These and other such approaches also differ from our concept, which is to utilize flexible or semi-rigid devices. Our fabrication methods differ to create our more flexible devices, which provide advantages for long-term use in the body. For instance, one can easily imagine the advantages of a flexible electrode array, rather than a rigid collection of penetrating electrode structures, to stimulate the spinal cord.

One of the main prior patents that is relevant to the present invention is Palanker, published 15 Sep. 2005, US #20050203601A1, also described in *J. Neural Engineering*, vol. 2, pp. S105-S120, 2005 by Palanker et al. from Stanford University. This application, entitled "Neural stimulation array providing proximity of electrodes to cells via cellular migration," differs from the present art in that the application claims an array of electrically conductive pillars on a substrate which includes silicon circuitry; thus, it is a rigid substrate, and the neural tissue must conform to it. The size of the array is limited due to the device's stiffness not allowing it to conform to the gross anatomical shape of the target neural structures. This is a problem for a retinal implant, for example, because the inner surface of the eye is curved. A very large array would sit as a chord across the arc of the inside of the eye wall, likely causing gross biocompatibility issues. In contrast, our array of electrically conductive pillars is on a thin, flexible substrate that can conform to the shape of the target anatomy. The flexible substrate also contains signal conductors which are encased in an inorganic thin film insulator to provide a protective and insulating barrier against the harsh biological environment of an implant. In one alternate embodiment, we have also invented a hollow post on a thin flexible substrate, in which the electrode materials are micro-fabricated at the bottom of hollow pillar that rests atop an enlarged chamber that surrounds the exposed electrode on the flexible array surface. This configuration provides several advantages. First, the area of the charge transfer (electrode) material can be made larger to allow a higher electrical current density through the smaller hollow pillar's top opening. This effectively increases the local current density; thus, for the same current density through the opening at the top of the post, the current density through the charge transfer (electrode) material is lower, thereby minimizing the risk of failure of the electrode material.

A second common problem with implanted electrodes that we have addressed in the present art is that the electrode materials can become fouled with protein or over-coated with glial cells over time after implantation. This is commonly known as a scarring response. The hollow pillars we propose in one embodiment also create distance between the target tissue and the electrode surface, and these pillars can also be pre-filled with conductive liquids or gets to inhibit electrode fouling by tissue reactions.

In general, the current approaches for fabricating micro-electrode arrays for all commercially available medical devices do not use modern micro-fabrication technology. The use of more traditional approaches to implantable electrode array fabrication (e.g., hand assembly) imposes a significant limitation on the number of electrodes that could be incorporated into devices. More modern micro-fabrication technology offers the possibility of delivering electrode arrays with potentially hundreds (or more) electrodes that could be addressed individually. For certain applications, especially within more complex systems like the visual system, there are significant potential advantages for using arrays with much greater numbers of electrodes than have traditionally been used. Use of micro-fabrication technology also makes it possible to create stimulation systems, in which the electrode array and stimulating modules are integrated, which differs significantly from all current devices that are made with more traditional methods involving hand-assembled packaged neuro-stimulation and neuro-modulation devices.

No admission is made that any reference cited herein constitutes prior art. Applicant expressly reserves the right to challenge the accuracy and pertinence of any cited documents.

SUMMARY

1st Variation of the Invention

The method of the present invention provides a way for interfacing with nerves or nerve cells, with an electrode array at least a portion of which is flexible and micro-fabricated and which can be used to permit or enhance Insertion into, conformal placement along, interdigitation within (including having the host tissue mold around), or wrapping around nerve tissue to stimulate, record or modify neuronal activity. The invention in one aspect does this with electronic and other components, some of which might lie external to the body, that together with the electrode array(s) form a neural prosthetic system that can: 1) wirelessly supply power to the internal electronics; 2) wirelessly transmit electrical commands and data to the Internal components to manage the power utilization of the internal components and the profile of electrical stimulation that is delivered to neurons; and 3) record biological parameters from said neurons. These functions can be performed in accordance with pre-programmed protocols or in response to commands generated externally by technical staff or by the patients themselves to optimize the prosthesis' performance. The adjustments in stimulus characteristics would be intended to create specific rehabilitative effects, such as enhancement of vision or hearing, muscle movement, bowel/bladder control, gait control, or to treat other neurological or psychiatric problems, including neural dysfunction in organs, like the heart.

The aforementioned micro-fabricated electrode array in one variation or embodiment can also include separate mechanical support structure(s) for the electrodes, which may exist as individual tines that contain one, or more than one, electrode site(s) along each tine. The precise design of the array/tines would be customized for the intended implantation site and will be designed to mate with a custom designed insertion tool to affect the surgical operation.

This micro-fabricated electrode array in a further embodiment can exist in part or in whole as a fimbriated structure such that the individual wires and the electrodes to which they are connected could move independently from adjacent wires and electrodes to facilitate the apposition of the electrodes around nerves or the three-dimensional insertion of the device within a part of the nervous system or an organ.

In a further aspect of the invention the micro-fabricated electrode array is designed to be placed in apposition to nerve tissue in a manner that influences the local neuronal environment to achieve proximity between electrodes and neurons to: 1) lower stimulation thresholds; 2) selectively stimulate certain neurons or neuronal pathways; 3) selectively inhibit certain neurons, or 4) otherwise modify the responses of nearby neurons with methods that include, but are not limited to:

a) use of geometrical shapes to align the stimulating and return electrodes in a manner that limits electrical interference between adjacent stimulating electrodes and achieves low levels of required electrical field strength to stimulate the target cells. The geometric designs could include, for instance, concavities or elevations along the various tines of the electrode array. A minimum of two electrodes would be distributed around the concavity (either atop the walls of the concavity or at the base of the concavity, or in some other distribution within or in the immediate vicinity of the concavity) to create a relatively well-confined electrical field (by using one electrode as a stimulating electrode and the other electrode as a current return electrode, or by using a large and proximal common current return electrode) that would envelop one or some small number (<20) of neurons to modify (either facilitate or suppress) the firing of the neurons that lie within the region of the relatively well-confined imposed electrical field. The spacing between the two stimulating and return electrodes around the small collection of neurons is close enough so that the intervening region is on the order of the size of one or a small number (20 or fewer) of target neurons.
  b) attracting neurons toward regions having a relatively well-confined electrical field by incorporating materials, surface modifications, geometric designs, bioactive substances, electrical stimuli or fields or other strategies to promote desired biological effects and favorably affect the local environment to enhance the ability to stimulate, record or modify neural activity.
  c) impeding fibrotic, glial or other biological reactions that might impair the desired stimulation of neurons by incorporating materials, surface modifications, geometric designs, bioactive substances, electrical stimuli or fields or other strategies to reduce or eliminate cells or scars from the intended area of stimulation of neurons.

In a further aspect of the Invention the micro-fabricated electrode array contains three-dimensional (i.e. both or either, elevated or depressed) elements, which may either be solid or hollow. The hollow variety may be pre-loaded with polymers (e.g., hydrogels), saline or other fluid, solid, or semi-solid compounds to improve the quality of the interface between the array and the neural tissue. These three-dimensional structures may also be placed atop significantly larger electrode regions, and in this case the hollow three-dimensional structures could serve to focus the electric fields emanating from/to the electrode sites. Either the solid or the hollow variety of 3D protuberance could be electrically insulated along the sides or within the hollow cavity along any portion of the length of the structure, with or without electrical insulation on the distal end or along any section(s) along the elevated structure.

2nd Variation of the Invention

In another aspect of the invention it provides a method of interfacing with nerves within the brain, comprising an electrode array at least a portion of which is flexible and micro-fabricated and which would be used to permit or enhance insertion into, conformal placement along, inter-digitation within (including having the host tissue mold around), or wrapping around nerve tissue to stimulate, record or modify neuronal activity.

In a further aspect of invention it includes electronic and other components, some of which might lie external to the body, that together with the electrode array(s) form a neural prosthetic system that can: 1) wirelessly supply power to the internal electronics; 2) wirelessly transmit electrical commands and data to the Internal components to manage the power utilization of the internal components and the profile of electrical stimulation that is delivered to neurons; and 3) record biological parameters from said neurons. These functions can be performed in accordance with pre-programmed protocols or in response to commands generated externally by technical staff or by the patients themselves to optimize the prosthesis' performance. The adjustments in stimulus characteristics would be intended to create specific rehabilitative effects, such as enhancement of vision or hearing, muscle movement, bowel/bladder control, gait control, or to treat other neurological or psychiatric problems, including neural dysfunction in organs, like the heart.

In a further aspect of the invention the aforementioned micro-fabricated electrode array that may also include separate mechanical support structure(s) for the electrodes, which may exist as individual tines that contain one, or more than one, electrode site(s) along each tine. The precise design of the array/tines would be customized for the intended implantation site and will be designed to mate with a custom designed insertion tool to effect the surgical operation.

In yet another aspect of the invention the micro=fabricated electrode array would exist in part or in whole as a fimbriated structure such that the individual wires and the electrodes to which they are connected could move independently from adjacent wires and electrodes to facilitate the apposition of the electrodes around nerves or the three-dimensional insertion of the device within a part of the nervous system or an organ.

In yet another aspect of the micro-fabricated electrode array is designed to be placed in apposition to nerve tissue in a manner that influences the local neuronal environment to achieve proximity between electrodes and neurons to: 1) tower stimulation thresholds; 2) selectively stimulate certain neurons or neuronal pathways; 3) selectively inhibit certain neurons, or 4) otherwise modify the responses of nearby neurons with methods that include, but are not limited to:
   a) use of geometrical shapes to align the stimulating and return electrodes in a manner that limits electrical interference between adjacent stimulating electrodes and achieves low levels of required electrical field strength to stimulate the target cells. The geometric designs could include, for instance, concavities or elevations along the various tines of the electrode array. A minimum of two electrodes would be distributed around the concavity (either atop the walls of the concavity or at the base of the concavity, or in some other distribution within or in the immediate vicinity of the concavity) to create a relatively well-confined electrical field (by using one electrode as a stimulating electrode and the other electrode as a current return electrode, or by using a large and proximal common current return electrode) that would envelop one or some small number (<20) of neurons to modify (either facilitate or suppress) the firing of the neurons that lie within the region of the relatively well-confined imposed electrical field. The spacing between the two stimulating and return electrodes around the small collection of neurons is close enough so that the intervening region is on the order of the size of one or a small number (20 or fewer) of target neurons.
   b) attracting neurons toward regions having a relatively well-confined electrical field by incorporating materials, surface modifications, geometric designs, bioactive substances, electrical stimuli or fields or other strategies to promote desired biological effects and favorably affect the local environment to enhance the ability to stimulate, record or modify neural activity.
   c) impeding fibrotic, glial or other biological reactions that might impair the desired stimulation of neurons by incorporating materials, surface modifications, geometric designs, bioactive substances, electrical stimuli or fields or other strategies to reduce or eliminate cells or scars from the intended area of stimulation of neurons.

In another aspect of the invention the micro-fabricated electrode array contains three-dimensional (i.e. both or either, elevated or depressed) elements, which may either be solid or hollow. The hollow variety may be pre-loaded with polymers (e.g., hydrogels), saline or other fluid, solid, or semi-solid compounds to improve the quality of the interface between the array and the neural tissue. These three-dimensional structures may also be placed atop significantly larger electrode regions, and in this case the hollow three-dimensional structures could serve to focus the electric fields emanating from/to the electrode sites. Either the solid or the hollow variety of three-dimensional structure could be electrically insulated along the sides or within the hollow cavity along any portion of the length of the structure, with or without electrical insulation on the distal end or along any section(s) along the elevated or depressed structure.

$3^{rd}$ Variation of the Invention

A method and system for interfacing with the retina, an electrode array at least a part of which is flexible and micro-fabricated and which would be used to permit or enhance insertion into, conformal placement along, interdigitation within (including having the host tissue mold around), or wrapping around nerve tissue to stimulate, record or modify neuronal activity wherein the array has:
   a) an assembly of electrodes surgically implanted into the sub-retinal space or onto the epi-retinal surface that can gradually become incorporated into, or which would allow/promote molding of the host tissue around the three-dimensional elements to achieve close proximity between the stimulating electrodes and retinal neurons;
   b) an associated assembly of return electrodes that are either on or in close proximity to the stimulating electrodes. These return electrodes could be used in a configuration to form a single electrical potential surface shaped in such a way to minimize or eliminate electrical cross-talk among electrodes;
   c) electrical circuits, including for example wires, coils, transistors, and photoactive elements, for driving the electrode assemblies to deliver electrical pulses and to create electrical fields in the vicinity of the target nerve cells;
   d) electrical circuits that can store and transmit information about the electrical impedance of the nerve tissue-electrode interface to an external controller;
   e) electrical demultiplexer circuits that will allow a relatively large number of electrodes to be addressed (e.g., to receive electrical stimulation or to record activity) by using only a small number of lead wires that enter the demultiplexer circuit; and
   f) external electronic circuits that can alter the stimulus profile to achieve more effective or safer patterns of neuronal activity according to feedback from clinicians, the patients themselves, or artificial intelligence incorporated in the control unit's firmware. The adjustments in stimulus characteristics would be intended to improve conscious or other sensory or sensorimotor defects, or e.g. to modify input to subconscious visual or other systems in the body that control, for example, circadian rhythms.

In a further aspect of the invention the aforementioned micro-fabricated electrode array on a flexible substrate may also include a separate mechanical support structure(s) for the electrodes, which may exist as individual tines that contain one, or more than one, electrode site(s) along each tine. The precise design of the array/tines would be customized for the intended implantation site and will be designed to mate with a custom designed insertion tool to effect the surgical implantation operation.

The method and apparatus of the present invention wherein the micro-fabricated electrode array is designed to be placed in apposition to nerve tissue in a manner that influences the local neuronal environment to achieve proximity between electrodes and neurons to: 1) lower stimulation thresholds; 2) selectively stimulate or record from certain neurons or neuronal pathways; 3) selectively inhibit certain neurons, or 4) otherwise modify the responses of nearby neurons with methods that include, but are not limited to:

a) use of geometrical shapes to align the stimulating and return electrodes in a manner that limits electrical interference between adjacent stimulating electrodes and achieves low levels of required electrical field strength to stimulate the target cells. The geometric designs could include, for instance, concavities along the various tines of the electrode array. A minimum of two electrodes would be distributed around the concavity (either atop the walls of the concavity or at the base of the concavity, or in some other distribution within or in the immediate vicinity of the concavity) to create a relatively well-confined electrical field (by using one electrode as a stimulating electrode and the other electrode as a return electrode, or by using a large and proximal common return electrode) that would envelop one or some small number (<20) of neurons to modify (either facilitate or suppress) the firing of the neurons that lie within the region of the relatively well-confined imposed electrical field. The spacing between the stimulating and return electrodes around the small collection of neurons is close enough so that the intervening space is on the order of the size of one or a small number (20 or fewer) of target neurons.

b) attracting neurons toward regions having a relatively well-confined electrical field by incorporating materials, surface modifications, geometric designs, bioactive substances, electrical stimuli or fields or other strategies to promote desired biological effects and that favorably affect the local environment to enhance the ability to stimulate, record or modify neural activity.

c) impeding fibrotic, glial, or other biological reactions that might impair the desired stimulation of or recording from neurons by incorporating materials, surface modifications, geometric designs, bioactive substances, electrical stimuli or fields or other strategies to reduce or eliminate extraneous cells or scars from the intended area of stimulation of neurons.

In a further aspect of the invention the micro-fabricated electrode array would contain three-dimensional (i.e. both or either, elevated or depressed) elements, which may either be solid or hollow. The hollow variety may be pre-loaded with polymers (e.g., hydrogels), saline or other fluid, solid, or semi-solid compounds to improve the quality of the interface of the array to the neural tissue. These three-dimensional structures may also be placed atop significantly larger electrode regions, and in this case the hollow 3D structures could serve to focus the electric fields emanating from or to the electrode sites. Either the solid or the hollow variety of three-dimensional structure could be electrically insulated along their sides or within the hollow cavity along any portion of the length of the structures, with or without electrical insulation on the distal end or along any section(s) along the elevated or depressed structure.

In yet another aspect of the invention the electrode array exists as part of a system that contains: photoreceptive or photoactive elements, which can exist either at the tips of the electrode tines or along the tines or at the base of the flexible substrate that can capture the energy of incoming light and convert this energy into electrical signals that can then be used to direct or influence the pattern and/or strength of electrical stimulation delivered to nearby neurons. The array and system would include the necessary electronic components (e.g., wires, coils, and/or transistors) to receive supplemental electrical power, control the distribution of electrical stimulation and the strength of electrical stimulation to neurons, conserve electrical power; and, detect, utilize and transmit digital information about the response of nearby neurons, the impedance of electrodes, or the relative level of light that is incident upon the photoreceptive elements. The information about the levels of incoming light detected within the retina, or any other feature of the information that is detected, could be used to influence the distribution or strength of electrical stimulation delivered through the adjacent stimulating electrodes. The stimulus parameters that are chosen for stimulation could be influenced by external commands that are sent wirelessly to the implanted device, which themselves may be influenced by information received by an external camera, sent to the external components (through wires or wirelessly), by the psychophysical responses of patients, or by the choices of medical personnel or researchers that could be used to make judgments about changes in stimulation or modulation parameters that the device would impart to the retina.

$4^{th}$ Variation of the Invention

In another variation of the invention it provides an interface for selectively making electrical contact to a plurality of neural cells in a biological neural network, said interface comprising: a) a flexible substrate having a thickness of less than 0.1 mm and consisting of metal conductors encased in a hermetic barrier layer further encased in one or more polymer protective layers; b) a plurality of electrically conductive posts extending from said flexible substrate, wherein top surfaces of said posts are facing away from said substrate can make electrical contact to said neural cells, wherein side surfaces of said posts are electrically isolated from surrounding neural tissue, and are electrically isolated from each other, In a further aspect the interface the metal conductors consist of evaporated Au having a thickness in the range of 100 nm to 3,000 nm, where the Au is coated above and below with a thin adhesion layer of Ti or completely wrapped in a thin adhesion layer of Ti.

In yet another aspect of the interface the metal conductors consist of Au deposited via physical vapor deposition (PVD) and having a thickness in the range of 100 nm to 10,000 nm, where said metal conductor is coated above and below with a thin adhesion layer of Ti or completely wrapped in a thin adhesion of layer of Ti. This could include a 10-100 nm thick layer of Pt on top of the Au, but under the top Ti adhesion layer.

In yet another aspect of the invention the metal conductors of the interface consist of Au coated above by Pt having a thickness in the range of 10 nm to 100 nm, where said metal Pt/Au bilayer is coated above and below with a thin adhesion layer of Ti or completely wrapped in a thin adhesion layer of Ti. The Pt provides a safety layer in that it can function as a stable charge transfer material, although of lower charge transfer capacity, in the event of a failure of the high charge transfer material layer which is preferentially SIROF.

In a further aspect the hermetic barrier layer is SiC, SiOC or a combination of or bilayer of SiC and SiOC.

In yet another aspect of the Interface the polymer protective layer consists of 1 micron to 25 micron thick layer of at least one of the following polymers: polyimide, silicone, polyurethane, parylene, polyethylene, polypropylene, peek, polyamide, polyester, PEEK, liquid crystal polymer, other polymers, or mixtures thereof.

In yet another aspect of the Interface the posts are 10 micrometers to 300 micrometers tall.

In yet further aspect of the interface the posts are roughly cylindrical and 5 micrometers to 100 micrometers in diameter.

In yet another aspect of the interface the posts are laterally spaced between 10 micrometers and 500 micrometers.

In yet further aspect of the interface the posts are roughly cylindrical in shape with a flat, rounded or pointed surface.

In yet another aspect of the interface the posts comprise a high charge injection material, preferentially SIROF, coated on an electrically insulating post.

5$^{th}$ Variation of the Invention

In yet another aspect of the Invention it provides an interface for selectively making electrical contact to a plurality of neural cells in a biological neural network, said interface comprising: 1) a flexible substrate having a thickness of less than 0.1 mm and consisting of metal conductors encased in a hermetic barrier layer further encased in one or more polymer protective layers; b) stimulating or recording electrode surfaces consisting of a high charge injection material; and c) a plurality of electrically non-conductive tubes or hollow posts extending from the electrode surfaces on said flexible substrate, wherein the outside surfaces, the top surfaces and the inside surfaces are electrically insulated from said neural tissue, and wherein the inner bottom surfaces of said posts make electrical contact to the interstitial neural fluid, and wherein said posts are electrically isolated from each other.

In a further aspect of the interface of the invention the metal conductors consist of Au deposited by physical vapor deposition and having a thickness in the range of 100 nm to 3,000 nm, where the Au is coated above and below with a thin adhesion layer of Ti or completely wrapped in a thin adhesion layer of Ti.

In yet another aspect of the invention the metal conductors of the interface consist of electroplated Au having a thickness in the range of 100 nm to 10,000 nm, where said metal conductor is coated above and below with a thin adhesion layer of Ti or completely wrapped in a thin adhesion of layer of Ti.

In yet another aspect of the invention the metal conductors of the interface consist of Au coated above by Pt having a thickness in the range of 10 nm to 100 nm, where said metal Pt/Au bilayer is coated above and below with a thin adhesion layer of Ti or completely wrapped in a thin adhesion layer of Ti. The Pt provides a safety layer in that it can function as a stable charge transfer material, although of lower charge transfer capacity, in the event of a failure of the high charge transfer material layer which is preferentially SIROF.

In another variation of the interface the hermetic barrier layer is SiC, SiOC or a combination of SiC and SiOC.

In another variation the polymer protective layer of the interface consists of 1 micron to 25 micron thick layer of at least one of the following polymers polyimide, silicone, polyurethane, parylene, polyethylene, polypropylene, peek, polyamide, polyester, PEEK, liquid crystal polymer, other polymers, or mixtures thereof.

In yet another aspect of the interface the high charge injection material consists of at least one of following, platinum, platinum black, titanium nitride, sputtered iridium oxide film (SIROF), anodic iridium oxide film (AIROF), electrodeposited iridium oxide film (EIROF), or thermal iridium oxide film (TIROF).

In yet another aspect of the interface the hollow post is of an overall height of between 25 micrometers and 300 micrometers.

In yet another aspect of the interface the hollow post consists of an outer diameter from 15 micrometers to 100 micrometers.

In yet another aspect of the interface the hollow post consists of an inner dome height of from 1 micrometer to 25 micrometers.

In yet another aspect of the interface the hollow post consists of an inner diameter of between 5 micrometers and 50 micrometers.

In yet another aspect of the interface the hollow post consists of a wall thickness of between 5 micrometers and 25 micrometers.

In yet another aspect of the interface the posts are laterally spaced between 15 micrometers and 400 micrometers center-to-center.

In yet another aspect of the interface the stimulating or recording electrodes each have an area of from 100 square micrometers to 150,000 square micrometers.

In yet another aspect of the interface each stimulating or recording electrode is covered by an insulating dome roof that is self-supporting.

In yet another aspect of the interface said electrode dome roof is supported by structures within the domed area.

In yet another aspect of the interface the electrode dome roof support structures consist of a set of pillars or posts.

In yet another aspect of the interface the electrode dome roof support structures consist of a set of radially-oriented support walls.

In yet another aspect of the interface the electrode dome wall thickness is between 5 micrometers and 25 micrometers and the electrode dome roof thickness is between 5 micrometers and 25 micrometers.

In yet another aspect of the interface electrode dome is created by removal of a sacrificial material and the sacrificial material can be polynorbornene or a photoresist.

In yet another aspect of the interface the hollow posts are filled with a conductive solution or get and be but is not limited to a conductive solution or get includes agents to inhibit ingress of cells and/or proteins. Alternatively, the conductive solution or get includes agents to promote ingress of neurons.

In another aspect of the interface the posts can be filled by evacuating a chamber to less than 1 mTorr, covering the hollow tubes with the desired solution or gel, and then slowly re-introducing an ambient pressure of from 760 Torr to 7,600 Torr to force the solution into the hollow posts and the electrode dome, if they are present.

Protecting the electrode surface of the interface from tissue/protein fouling by means of deploying a long hollow conductive solution-filled tube over the electrode surface is used.

In another aspect of the interface it provides for directing and focusing electrical current a distance away from the electrodes by means of a hollow insulating tube filled with a conductive medium fabricated over each electrode is used. The conductive medium can be isotonic saline solution or a artificial interstitial fluid. Additionally, the conductive medium can contain neurotrophic factors to promote neural growth. Alternatively, the conductive medium can contain factors to inhibit neural growth. Additionally, the conductive medium can contain ionic content to improve conductivity. In another aspect the conductive medium can contain chemicals to inhibit the passage of proteins and/or biological tissue.

In yet another aspect of the invention the flexible substrate on which the interface is micro-fabricated can be terminated with a set of connection pads for bonding to another flexible circuit or a connector via wire bonding, gold bump bonding, ball bonding, thermo-compression bonding, or any number of other interconnection means. The flexible substrate may also be integrated as part of a larger flexible circuit that provides means for interconnecting the various components of an implantable neuro-stimulation or neuro-modulation system, such as a sealed hermetic package containing electronic components, one or more RF coils to provide power and/or data communication, and surgical mounting or suturing hardware.

6$^{th}$ Variation of Invention

In another variation of the invention it provides a retinal prosthesis for treatment of diseases of the outer retina, the prosthesis having: a) an assembly of drive electrodes surgically implanted in the sub-retinal space that retina tissue molds around to achieve close proximity between the cells of the inner retina and the drive electrodes; and b) an associated assembly of return electrodes in close proximity to the drive electrodes known as the return electrodes, which may be connected together to form a single electrical potential surface, or may be a single solid or perforated conductor; c) an electrical circuit for driving the electrode assemblies to achieve short impulses of electrical field in the vicinity of the target cells by applying charge-balanced stimulation current pulses; d) geometrical placement of the drive and return electrodes so as to limit interference between adjacent drive electrodes; e) geometrical placement of the drive and return electrodes so as to achieve low levels of required electrical field strength to stimulate the target cells; and f) an electrode drive method, comprising a bi-phasic current pulse shape that will reliably excite nearby neurons but will not create long term harmful biological reactions in the target tissue.

7$^{th}$ Variation of Invention

In another variation of the invention it provides an apparatus for exciting neurons which includes: a) a stimulation system that is designed and built so that the spacing between at least one drive and at least one return electrode for each neuron is close enough together so that the intervening space is on the order of the size of the target neurons; b) the shaping of the drive and return electrodes for each neuron is such that the intervening electric field is mostly confined to the vicinity of the target neuron or neurons, such that a limited number of cells (one or more) will be stimulated; c) where the drive and return electrodes are positioned such that the most sensitive part of the target neuron, which is near the initial axonal segment, is in the intervening space between the two electrodes; d) the electrical pulses used for stimulation are shaped so that the minimum energy required is used to excite the target neuron; e) the geometric shape of the drive and/or return electrodes is such that over time, the target neural tissue molds itself around said electrodes with a minimum of glial cell growth in the area of electrode placement; and f) an electrode drive method is used that comprises a pulse shape that will reliably excite nearby neurons but will not create long term harmful biological reactions.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

FIG. 38 is a schematic diagram of a variation of the embodiment of the electrode structure of the electrode structure of FIG. 3A;

Figure 1:
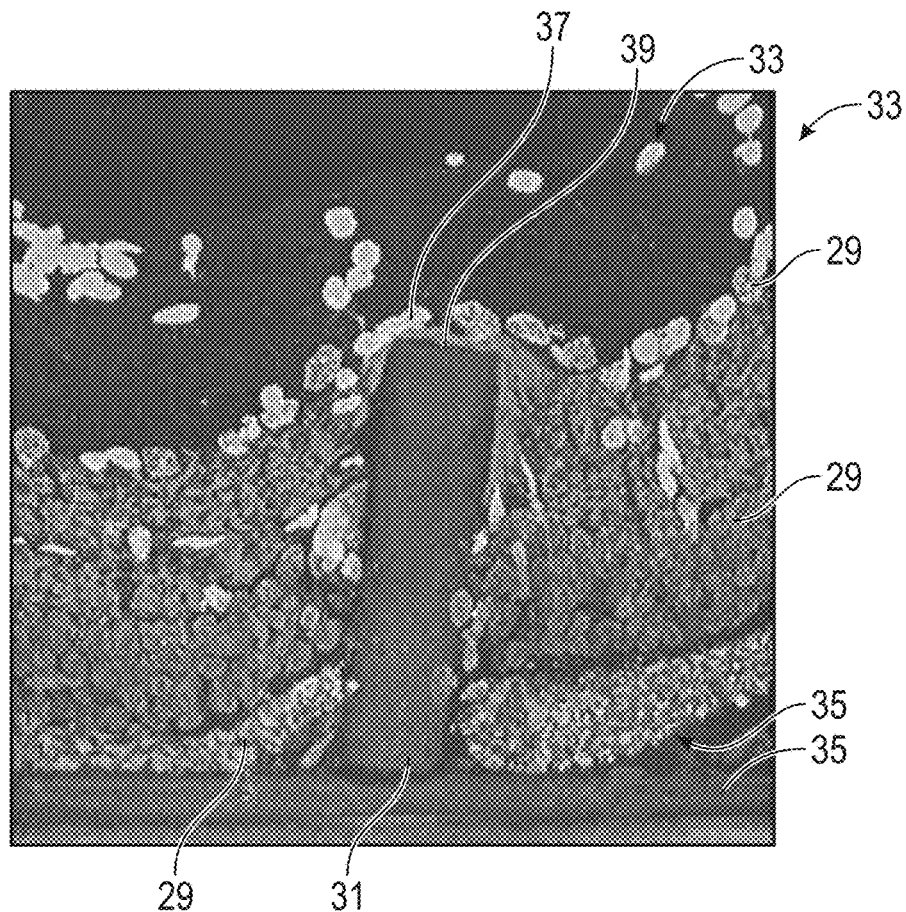
FIG. 1 is a picture of an histological slide of a mini-pig retina tissue that has molded around a three-dimensional micro-fabricated electrode post.

Additional features and advantages will be set forth in the detailed description which follows, and in part will be readily apparent to those skilled in the art from the description or recognized by practicing the embodiments as described in the written description and claims hereof, as well as the appended drawings described above.

DETAILED DESCRIPTION

The present invention describes various devices and methods for delivering stimulation more safety to a relatively larger number of small clusters (even individual neurons) of nerve cells than can be achieved with traditional or even more advanced micro-fabrication strategies that have been used or proposed to date. Inevitably, micro-fabrication methods must be used to create the large density of stimulating electrodes that will be needed to restore complex neurological functions. The smaller diameter electrodes that can be created with micro-fabrication methods can produce electrodes that are on the order of the size of the neurons that are the intended sites of stimulation. These two features of micro-fabricated devices make it possible to both stimulate a larger number of neurons (because of the large number of electrodes) and also to more selectively stimulate neurons (because of the smaller size and proximity of the electrodes to the neurons). The electrodes could even be made small enough to deliver stimulation to sub-cellular components of neurons, like the axon hillock region, which is known to be the site of lowest stimulation threshold for neurons.

This specification provides a number of approaches to solving the problems discussed above Including two related approaches to use micro-fabrication technology to achieve proximity to nerve cells that lie substantially beneath a neural surface. (The term "substantially" must be considered with respect to the part of the nervous system that is the intended site of stimulation. For the retina, neurons of interest lie roughly 30 microns below the surface, but the total cross-sectional depth of the retina is at most 300 microns. For the brain, the cortical neurons are 3-4 millimeters below the surface, but the thickness of the brain is several centimeters.) in one embodiment, we describe the use of microfabrication technology to create ultra-thin (≤75 microns thick) and flexible electrode arrays to stimulate neurons that lie deep within the brain (i.e. below the cortical neurons that lie within 3-4 millimeters of the surface of the brain). Reaching the deeper neurons with an ultra-thin device cannot be achieved by advancing the array into the nerve tissue because such arrays lack intrinsic rigidity. As such, insertion of such arrays requires use of a stiffener or support structure, or an insertion tool that can introduce and then leave the electrode array behind deep in the brain tissue.

In another embodiment, we describe the use of microfabrication technology to create relatively rigid tines on a flexible substrate. (prior micro-fabricated electrode arrays with three-dimensional structures have been made on rigid structures.) The presence of a flexible substrate will enhance the ability of the array to match the contour of a curved surface (like the retina) or a convoluted surface (like the brain). Although the tines of these flexible arrays could be introduced into the brain by external force (as has been done by Normann et al. with an hydraulic insertion device for use in the cortex of the brain), we suggest in the invention described herein that our array could become embedded over time into tissue that has molded itself through or around the tines, perhaps partially assisted by local pressures that can foster a more gradual introduction of an array into nerve tissue (as compared to the sudden insertion of an array into brain tissue by an hydraulic device or by some other such means).

A further extension of this concept relates to the use of particular geometries, surface modifications, biologically active devices, electrical fields or other means to attract neurons closer toward the stimulating electrodes. The goal would be to reduce stimulation thresholds by reducing the separation between neurons and stimulating electrodes. Taken to another level, this approach could be used to attract neurons not only to the vicinity of a stimulating electrode but within an electrical field that is highly focused. This approach, which in one embodiment could be achieved by having a stimulating and a return electrode around a divot along a tine into which neurons were attracted, would not only lower stimulation thresholds but would also enhance the selective stimulation of a subset of neurons, which as stated above, would help to achieve more selective neurological stimulation leading to functional rehabilitation, such as the restoration of vision.

These concepts could be applied to any type of nerve tissue, and thus would offer the possibility for restoration or modification of many types of neurological functions. To achieve these broad goals, the electrode arrays would have to exist as part of a neural prosthetic system, which could: 1) deliver the necessary power to drive electrodes; 2) provide the electrical Intelligence to control the stimulation to individual electrodes; and 3) be able to modify the stimulation parameters based upon external or internal Inputs, like those that might be given by a patient or in response to alterations in electrode behavior that could be detected by the electronics. As such, the electrode arrays described above would have to be integrated with a sophisticated electronic system, which would ideally operate wirelessly. This system could also be used to sense internal parameters, either biological or electrical (e.g. activity of local neurons or electrical impedance of electrodes), and transmit these parameters to external devices that would assist in the diagnosis of electrical or biological problems that might alter or negatively Influence the function of a neural prosthesis based on these concepts.

Justification for Molding Tissue Around Electrodes

Numerous Investigators have noted substantial differences between in vitro and in vivo neural stimulation threshold currents; this raises concerns for practical prosthetic designs. The effect is due primarily to the difference in electric field strength presented to the target cells in the two different experimental modalities. If in vitro—like thresholds could be achieved in a practical prosthesis, many potential system problems (e.g., potential neural damage, electrode corrosion, and limited stimulation specificity) could be greatly lessened.

The nature of body tissue into which electrode arrays are implanted is very different electrically from a saline solution. A model of the tissue as a fairly dense collection of dielectric spheres (the cells) surrounded by saline solution is more appropriate. A problem with this model, however, is that the interstitial saline, being an electrolyte, might not support the desired electrical fields. However, in experiments measuring far field current spreading, we do measure a resistive drop, indicating a resistive path through the tissue; thus, the tissue can in fact support an electric field. While there is more ionic content than just NaCl in interstitial fluid (ISF), an isotonic saline solution has a resistivity that is many orders of magnitude higher than a metal. Thus, ISF is not likely to form a short circuit across tissue especially when it makes up only 10-30% of the total volume depending on location.

As a first approximation, we assume that the far field arising from a stimulated electrode in an in vivo experiment is a classical point source field, i.e.:

$$E_F = \frac{Q}{4\pi\varepsilon} \cdot \frac{1}{r^2} \qquad (1)$$

We also assume that an in vitro experimental setup may be approximated by two circular plate electrodes of diameter D separated by a distance r. Assume r is small compared to D, in which case we have an inter-electrode field given by:

$$E_N = \frac{Q}{\varepsilon A} \text{ where } A \text{ is the area of the electrode.} \quad (2)$$

We can write (2) as $$E_N = \frac{4Q}{\varepsilon \pi D^2} \quad (3)$$

Taking the ratio of (1) and (3) we get $$\frac{E_F}{E_N} = \frac{1}{16} \cdot \left(\frac{D}{r}\right)^2 \quad (4)$$

This tells us that the near field is greater than the far field as long as r>D/4.\

On the one hand, a typical in vivo experiment might utilize a 400 micrometer diameter electrode that is 50 micrometers from its target cell. On the other hand, a typical in vitro experiment might utilize a 10 micrometer diameter electrode that is 2 micrometers from its target cell. In this case r/D=50/10=5, indicating that there would be a factor of 20 advantage in electric field strength in the in vitro case. This simple model, however, does not fully explain the large discrepancy in stimulation thresholds that is observed experimentally in the two cases.

In the parallel plate, near field electrode situation, a uniform field (i.e., potential gradient) exists between the plates regardless of the conductivity of the bordering intercellular fluid. It therefore guarantees a high electric field in the small space between a stimulated electrode and its current return electrode.

We propose to take advantage of the near field electrode's higher potential gradient and higher current density in the following manner. A micro-fabricated electrode array built on a flexible planar substrate having three-dimensional structures around which neural tissue will mold (as opposed to penetrating such neural tissue) will generate the higher potential gradients (and lower stimulation thresholds) that we desire. Further, if the three-dimensional structures were hollow and contained wells, factors could be added to encourage the growth of neuronal cells into the wells. The top of the wells could be an overlapping edge, and a stimulating electrode can be formed on the well's inner side and/or top, with the counter or current return electrode located at or near the bottom of the well. This gives the favorable near field situation enjoyed by in vitro experimentalists, and a high degree of isolation from neighboring cells as well. Further, one could also conceive of a larger-area planar electrode surface that could be covered with a three-dimensional dome structure, and a central hollow well. In this manner, the current density at the planar portion of the electrode array could be minimized, while focusing the current at the well's top surface (which would presumably be in intimate contact with the target neural tissue.)

The basic concept outlined herein has been experimentally verified since its initial conception in 2006. In FIG. 1, we demonstrate by differential staining the different types of cells 29 that surround an electrode post 31 that mini-pig retinal tissue 33 was allowed to mold itself around. While this result doesn't by itself guarantee functional synaptic junctions between the electrode and its neighboring neurons, it does rule out a completely non-functional gliotic scar that would render the electrode electrically Isolated from the tissue it was intended to stimulate.

FIG. 1 is an histological slide of mini-pig retina tissue 33 that has molded itself around a three-dimensional electrode post 31 that was micro-fabricated on top of a flexible polyimide substrate 35. The stains Mab30 and DAPI were used to highlight the retinal structures 29. Post 31 is 30 microns in diameter and 70 microns tall. Note the close apposition between the retinal neurons 37 and the top of the post 39, and the near absence of gliosis that would increase the impedance of the electrode-tissue interface.

One of the exciting possibilities of our approach is that if in vitro—type thresholds are possible with micro-fabricated structures and/or wells on the scale of the electrode in FIG. 1, the way is paved to construct very high resolution arrays with little crosstalk between channels. Therefore, it may be possible to fabricate such an array and implant it in a diseased retina as part of a system to restore high quality vision to the large population of patients who suffer from retinal degenerations.

Figure 2:
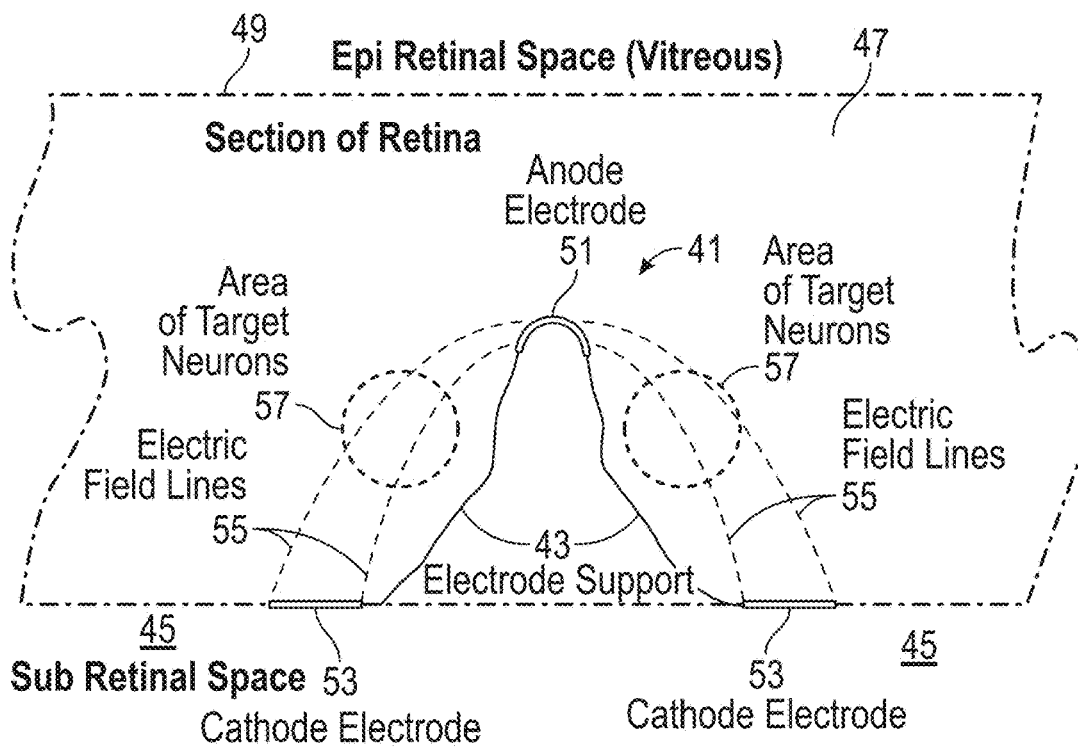
FIG. 2 is a schematic diagram of one embodiment of an electrode structure of the present invention embedded in retinal tissue.

In FIG. 2 is a cross-sectional schematic diagram of on variation of the electrode structure 41 of the present invention that provides one possible embodiment of a portion of which includes an electrode support 43. It has been surgically implanted in the sub-retinal space 45 of an eye, though the retina is only one possible location in which such an electrode could be used; the electrode is shown penetrating into the retina 47, but not exiting on the epi-retinal side 49. Two possible electrically-active portions of this electrode system are labeled "Anode Electrode" 51 and "Cathode Electrode" 53.

In the embodiment depicted in FIG. 2 the electrode structure 41 focuses the electric field lines 55 in a small region surrounding the electrode support 43, around which the host tissue, the target neurons, 57 have molded.

The intention of the design is to place the target neurons 57, which are the remaining healthy bipolar and ganglion cells, into close proximity with the electric field lines 55 radiating between the electrodes 51 and 53. This will cause the charge carriers which are in the vicinity of the neurons to migrate toward the oppositely charged electrode. This will disturb the normal resting potential of the cell, causing it to depolarize and thus generate a biological signal that will propagate down the axon of the target neuron. The divergence of the field in the vicinity of the target neurons will lower the field strength and hence the required input signal strength required to depolarize the target cells.

The localized return is a feature that makes this embodiment better confine the stimulation current (and thus the electric field). This feature will effectively shield the fields of adjacent similar electrodes from one another, thus allowing higher resolution stimulation than is possible with the conventional "uni-polar" design, which employs a common distant return for all electrodes.

Another advantage of the nearby return over the distant return is that high-resistance body tissues, such as the RPE layer in the eye, are not in the electric current path. This causes less required signal strength for stimulation than would otherwise be required in order to overcome this high resistance tissue.

The penetrating aspect of the electrodes will put them in close proximity to the target cells. This is important for obtaining low required signal strength for depolarizing the cells, since the field strength, which is the force per unit charge exerted on the charge carriers, is inversely proportional to the square of the distance from the field-generating charges on the electrodes.

Figure 3A:
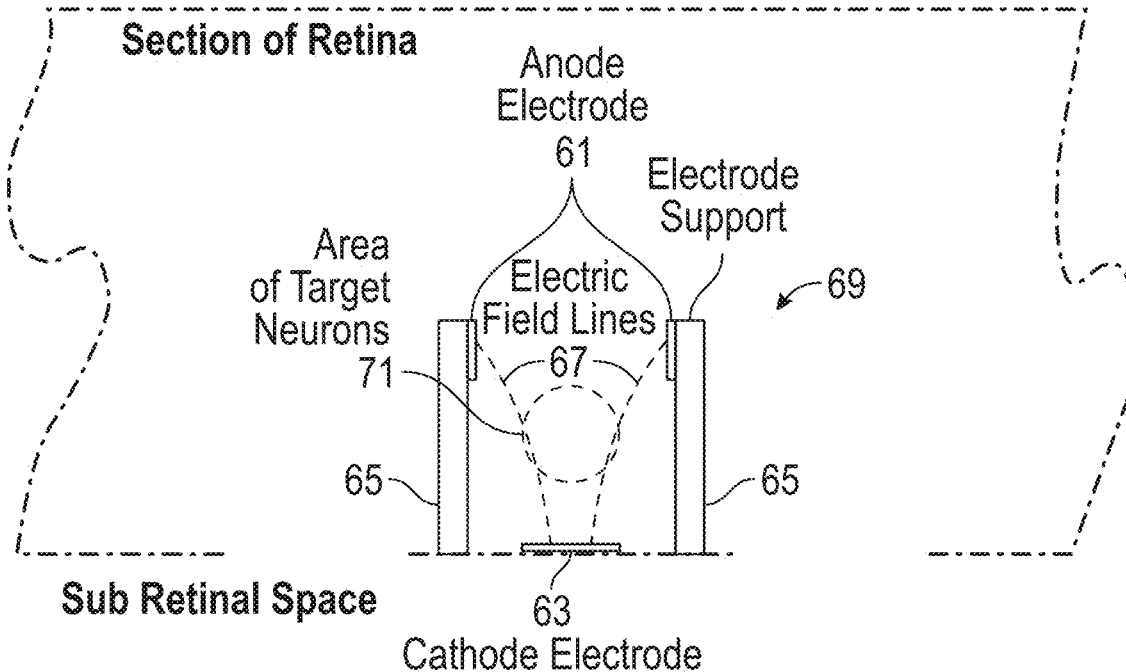
FIG. 3A is a schematic diagram of another embodiment of an electrode structure of the present invention embedded in retinal tissue.

FIG. 3A shows an alternative electrode embodiment shown in cross-section that encloses the electrodes 61 and 63 in a supporting structure 65 a hollow cylinder, thus further confining the field lines 67 and possibly lowering the required excitation field strength. The idea of an enclosing well 69 into which neuron growth 71 can be coaxed is not new, but the proposed idea combines this structure with the near and enclosed electric field 67, which is essential to the functional prosthesis.

Figure 3B:
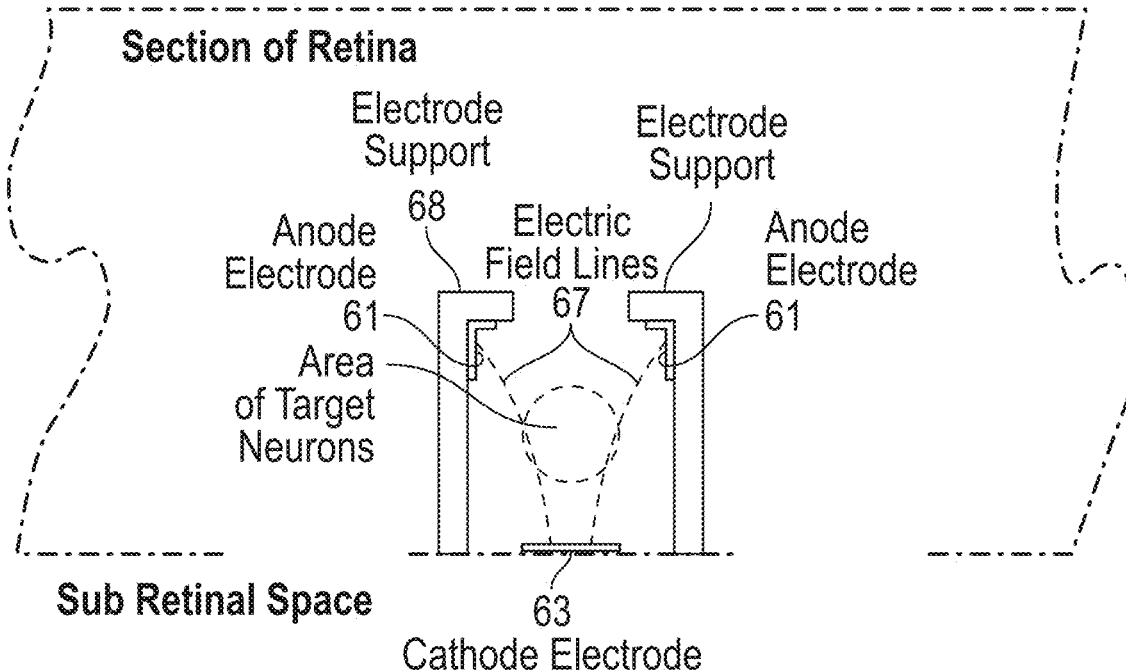

FIG. 38 shows another alternate embodiment of an electrode structure that also focuses the electric fields arising from current stimulation within a limited region surrounding the electrode support. In this particular embodiment, the electrode support a hollow cylinder with a flange 68 at its top opening; it is shown in cross section in FIG. 3B. Other electrode supports, such as the single solid post of FIG. 1, are also possible embodiments.

Other variations on the electrode supporting structure are also possible, such as varying the exact position of the electrodes on or under the supporting structure but maintaining close proximity between anode and cathode electrodes. Detailed structures of additional embodiments are discussed below.

Figure 4A:
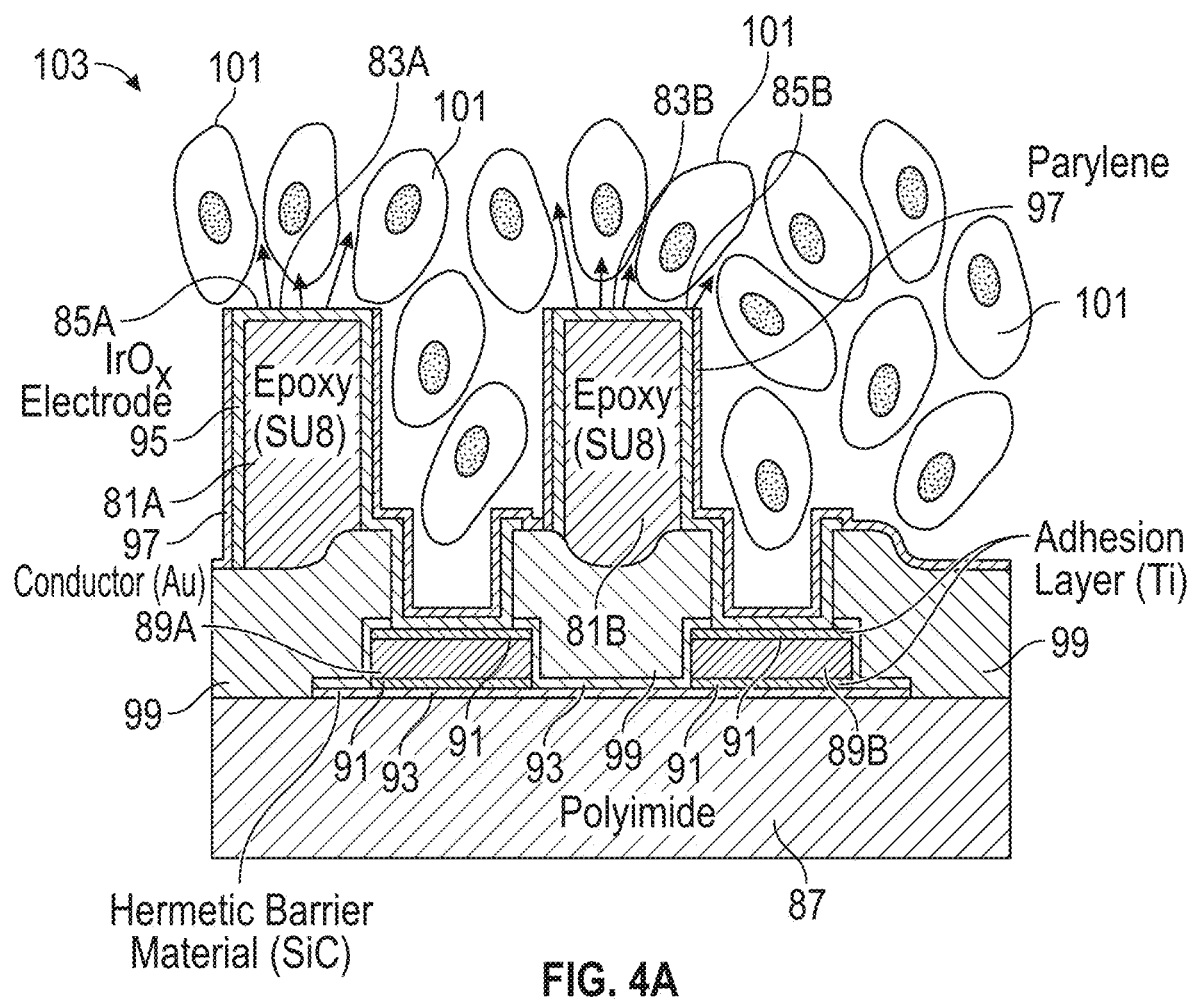
FIG. 4A is a schematic diagram showing the micro structure of another embodiment of the electrode structure of the present invention.

FIG. 4A is a cross-sectional view of a micro-fabricated electrode structure or interface 103. The parts or interface or structure 103 includes solid posts 81A and 81B with an electrodes 83A and 83B on their respective top surfaces 85A and 858. The entire structure sits on a flexible substrate 87 made of polyimide. On top of the flexible substrate are two conductive layers 89 A and 898 sandwiched between adhesion layers of titanium (Ti) 91, which in turn is encased in a hermatic layer 93 of silicon carbide (SIC). Titanium layers 91 connect to conductive layers 95 of iridium oxide (IrOx). The IrOx is encased in a layer of parlene 97, with the exception of the portion of the IrOx layer at the top 85A and 858 of and the superstructure of each post 81A and 81B. Posts 81A and 81B are made of photoimageable epoxy such as SU8 by MicroChem or other electrically non-conductive structural material. The balance of the structure 99 in FIG. 4A is made of polyimide.

As depicted in FIG. 4A neural tissue or neuron cells 101 have grown around and between posts 81A and 81B. Thus, the structure 103 froms an interface with the surrounding tissue or cells 101.

Figure 4B:
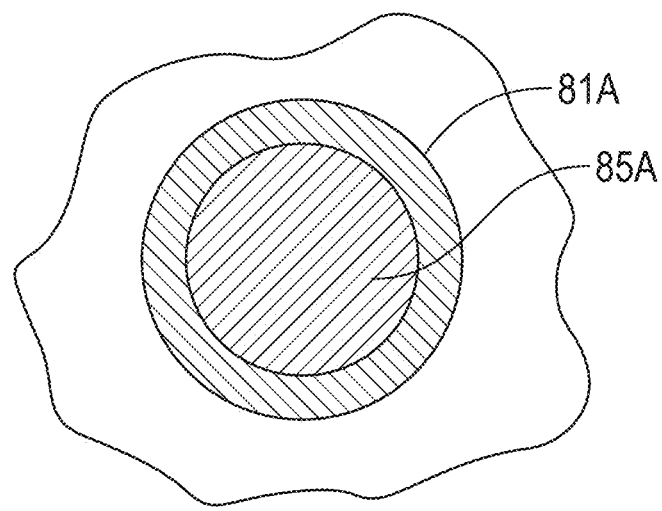
FIG. 4B is a top view of an electrode post depicted in FIG. 4A.

FIG. 4B shows a top view of one of the posts 81A which shows the post is cylindrical in shape. However, the post could be square on top and in the shape of a parallelepiped.

Referring back to FIG. 4A in a preferred embodiment conductive layers 89A and 898 are metal conductors which can be fabricated with different materials, but in this embodiment are evaporated Au having with a thickness in the range of 100 nm to 10,000 nm, where the Au is coated above and below with a thin adhesion layer of Ti or completely wrapped in a thin adhesion layer of Ti. Hermetic barrier layer 91 can be any suitable material including SIC or a combination of SiC and SiOC. The protective layer 97 in the preferred embodiment is a polymer protective layer of 1 micron to 25 micron thick layer of at least one of the following polymers: polyimide, silicone, polyurethane, parylene, polyethylene, polypropylene, peek, polyamide, polyester, PEEK, liquid crystal polymer, other polymers, or mixtures thereof.

The dimensions of the posts 81A and 81B can vary depending on the need or application. In various embodiments the posts can be 10 micrometers to 300 micrometers tall, roughly cylindrical from 5 to 100 micro meters in diameter. Posts 81A and 81B can be spaced laterally from 10 to 500 micrometers apart. Although the electrode partion 85A and 85B of each post is flat, the electrode surface could also be rounded or pointed in shape.

Conductive layer 95 that connects to the metal layer 89A and 89B as noted. Conductive layer 95 can be made from a high charge injection material. The following materials can make up the conductive layer platinum, platinum black, titanium nitride, SIROF, anodic iridium oxide film (AIROF), electrodeposited iridium oxide film (EIROF), or thermal iridium oxide film (TIROF). For most films including IrOx the preferred embodiment uses an adhesion layer of titanium atop the underlying conductors.

Figure 5:
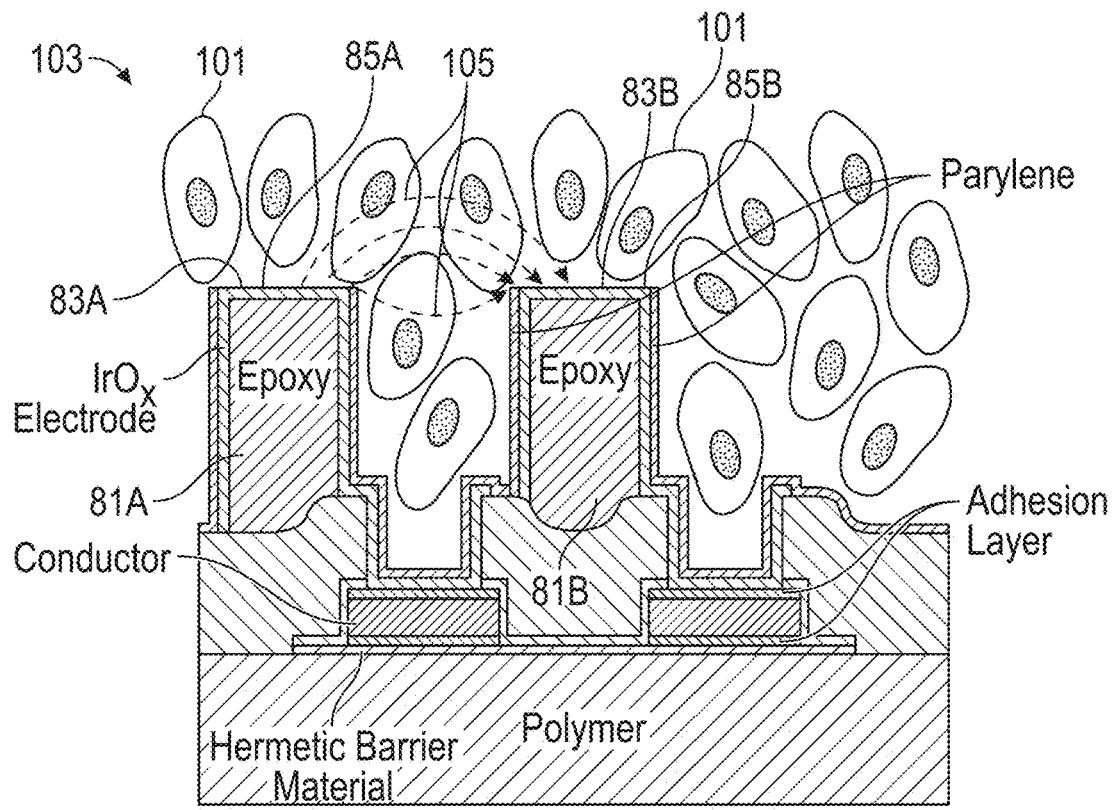
FIG. 5 is a schematic diagram of the electrode structure or interface structure depicted in FIG. 4A configured to generate a near electrical field.

FIG. 5 is a schematic diagram of electrodes structure 103 configured to produce a near electrical field that would extend within a range of 500 µm or less between the anode and cathode. Electrode 83A on the top surface 85B of post 81 and he acts as the anode and electrode 838 on the top of surface 85 a post 818 as the cathode. Neuron cells 101 has grown around posts 81A and 81B are stimulated by electrical field 105 created between the anode and cathode. It will be noted in more detail elsewhere herein the electrical fields generated can be biphasic and thus each electrode pair can be a cathode or an anode alternatively as the case may require.

Figure 6:
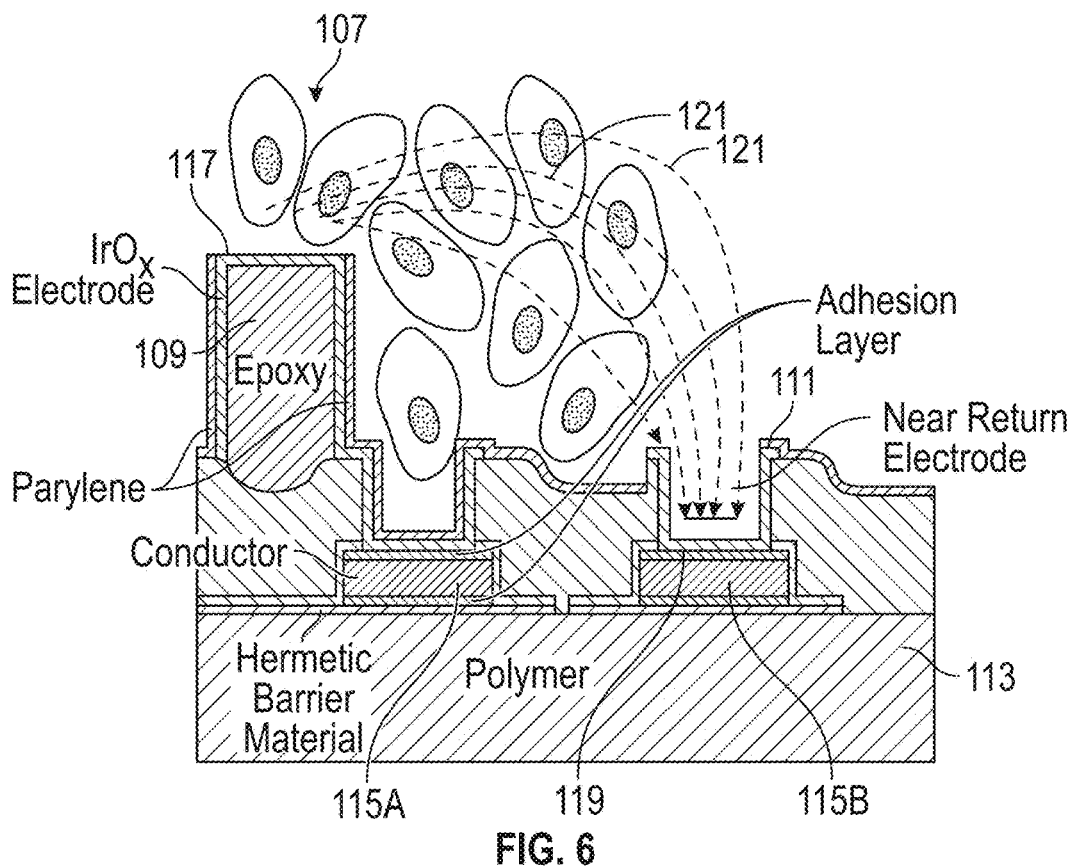
FIG. 6 is a schematic diagram of another embodiment of the electrode structure configured to generate near electric field.

FIG. 6 provides a schematic diagram of another embodiment of the interface 107 with on electrode on post 109 and second electrode 111 forming a substantially planar surface above flexible substrate 113. Interface 107 is made of the same materials as interface 103 in FIG. 4A and the difference in FIG. 6 being electrode 111 is a substantially planar metal layer that connects directly to metal layer 1158. In the variation shown in FIG. 6 exposed conductive layer 117 acts as the anode and exposed conductive layer 119 of electrode 111 acts as the cathode. As noted in a biphasic mode each electrode will alternate between a cathode and anode state. Field lines 121 represent the near electrical field pass from electrode 117 to electrode 119.

Figure 7:
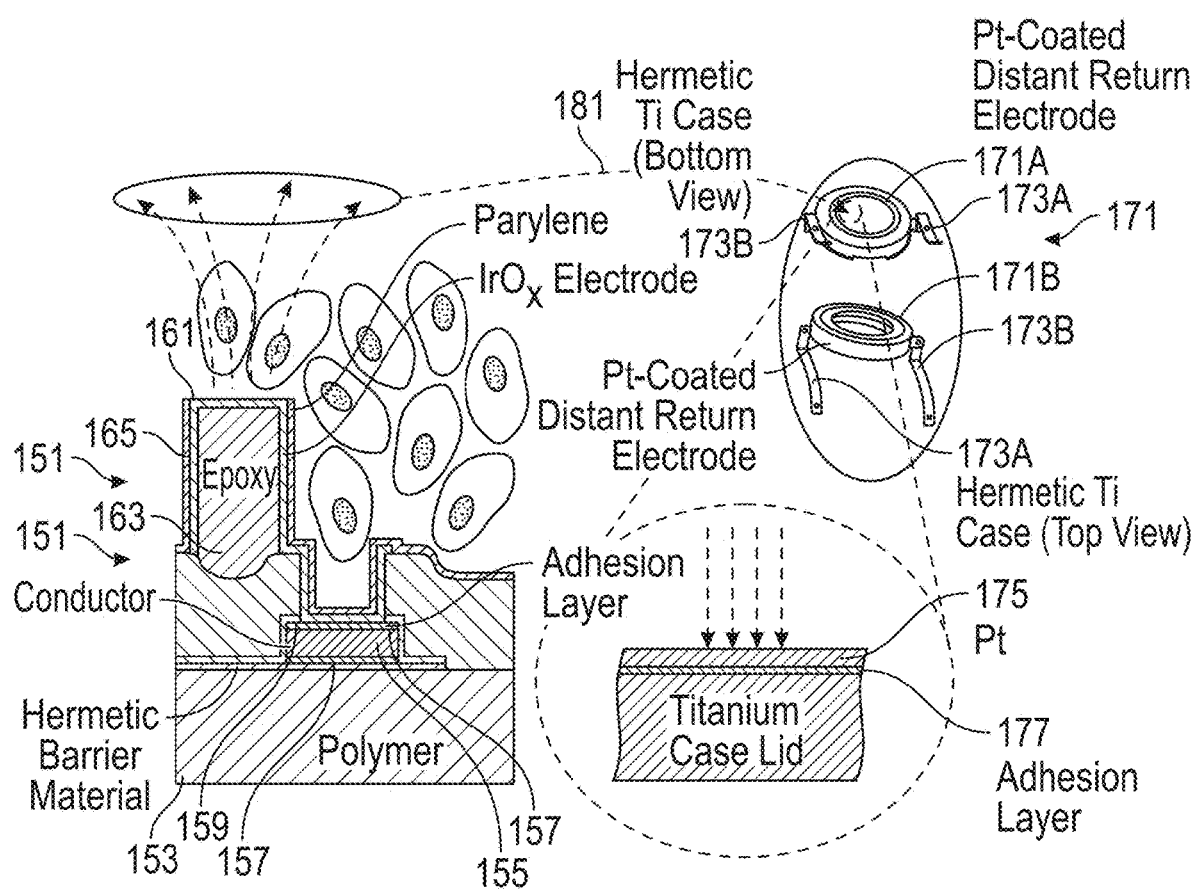
FIG. 7 is a schematic diagram of an embodiment of the electrode structure or interface configured to generate a far electric field.

FIG. 7 provides an example of an embodiment of the electrical interface structures of the present invention configured to create a far electrical field, one where the field covers a distance of up to one inch between the pair electrodes. In FIG. 7 electrode structure 151 the same as that depicted in FIG. 4A and FIG. 5 in structure and material composition. Electrode structure 151 consists of flexible substrate 153 in the preferred embodiment no more than 0.1 mm thick with metal conductive path 155, in the preferred embodiment gold (Au) sandwiched between adhesive layers 157 of titanium (Ti). Post 163 is made of an electrically insulating material that provides support, in one embodiment it can be made of an epoxy designed to provide the necessary support. Post 163 is covered by conductive layer 159 which is covered by insulating layer 165 where it makes contact with metal layer or conductive path 155 and up the sides of post 163. Conductive layer 159 is exposed at the top 167 of post 163 to form and electrode that makes contact with interstitial fluid and neurons 101 that have grown around interface structure 151. Within about an inch of interface structure 151 making electrical contact with the same neural tissue that has grown around interface structure 151 is a second electrode structure which is on 171.

In the aforementioned embodiment, the second electrode is the hermetic Ti case lid coated with a layer of sputtered or evaporated Pt having a thickness of between 10 nm to 100 nm and undercoated with a thin adhesion layer of Ti (as shown in the inset cross-section).

171 is a metallic package contains stimulating electronics in addition to serving as the return electrode which forms a paired electrode structure with 151 and generates an electrical field 181 and thus resulting current flow between them to thereby stimulate the nerve cells between them. Package 171 has suture tabs 173A and 173B. 171A is the bottom of metallic package 171 and 1718 is a top view of metallic package 171. Metallic package 171 in one embodiment is approximately 3 mm thick and approximately 12 mm in diameter. As indicated the bottom 171A inside surface of package 171 has a conductive layer 175 held on the titanium case lid 179 by adhesion layer 177.

Figure 7A:
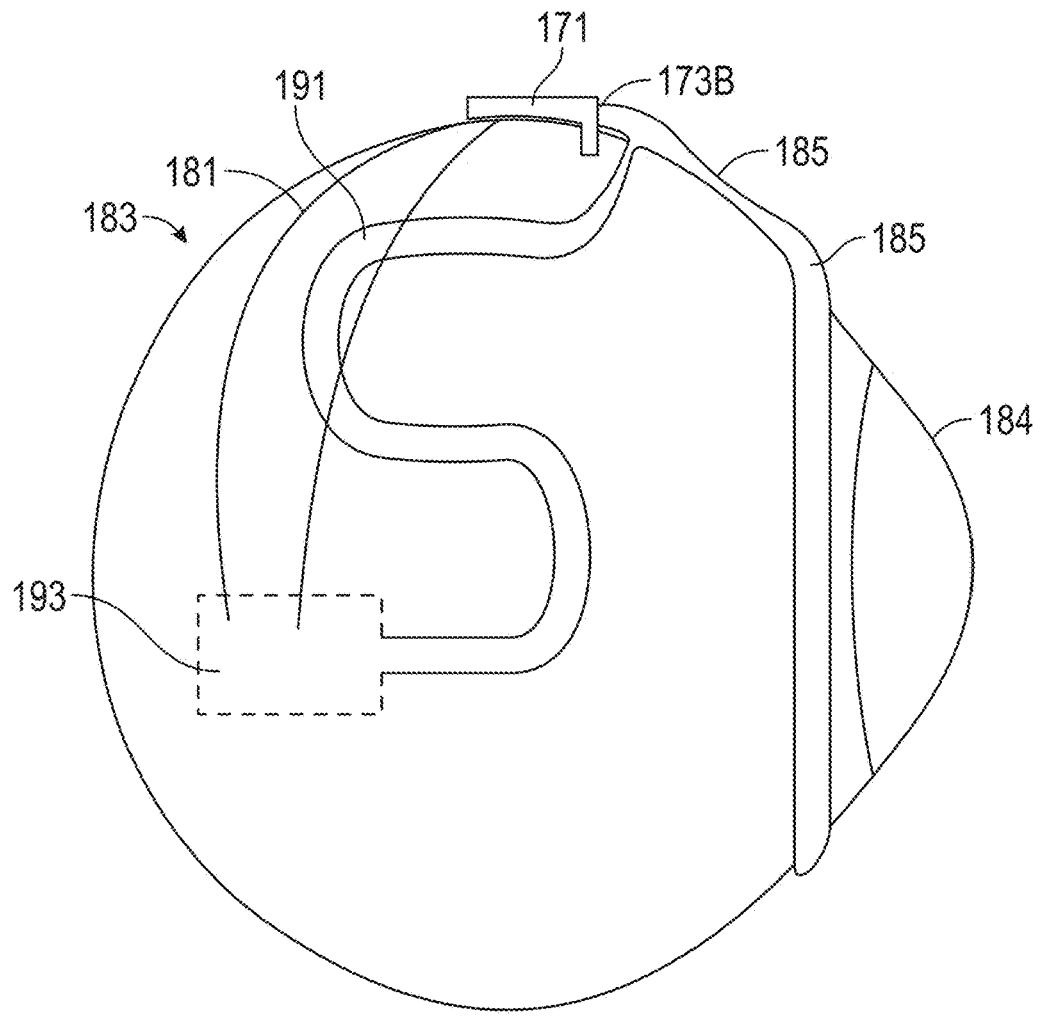
FIG. 7A is a schematic diagram of the electrode structure of FIG. 7 implanted on a patent's eye to restore or improve sight.

Referring to FIG. 7A, a schematic diagram of how the electrode structures would be implanted on a patient's eye ball 183 to help restore sight is shown. A side view of the eye ball is presented and the cornea 184 is to the right. Metallic package 171 is positioned on the top of the eye ball 183 with its bottom 171A with electrically conductive surface 175 resting on the top of the eye. Suture tab 173A is visible. The Pt coated electrode 175 makes electrical contact with the top of the eye ball and sits in the space between the top of the eye ball and the eye socket. Metallic package 171 connects by lead wires 185 to radio frequency coil 189 and by lead wires 191 to electrical interface array 193. Electrical interface array 193 is a structure that consists of a matrix of multiple electrical interfaces the individual interface 151 is depicted in FIG. 7.

Referring back to FIG. 7A when electrical stimulation is generated between the electrode on the metallic package and electrical interface array 193 the far electrical field 181 is created between the array 193 and the electrode 175 of metallic package 171. Coil 185 provides an avenue to provide power and data to metallic package 171 so that it can generate electricity to create the stimulating electrical field 181, since power and data would be provided wirelessly to the electronics within the metallic package 171. In the embodiment depicted coil 185 sits on the front hemisphere of the eye surrounding the cornea, but it is surgically placed behind the conjunctiva, which is the tent-like tissue that attaches to the perimeter of the cornea, and in front of the attachment points of the muscles which move the eyeball. The coil after being implanted is generally hidden by the 'curtain' of tissue that covers the front of the space between the eyeball 183 and the eye socket not shown.

Figure 7B:
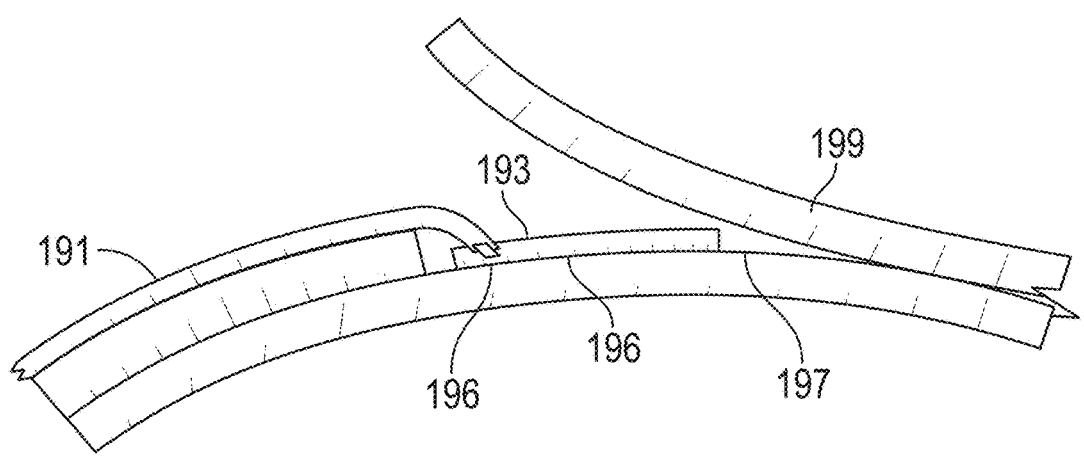
FIG. 7B is a schematic diagram of how and where the electrode interface array is implanted in the patients eye.

In FIG. 7A the electrode interface array, which is a matrix of electrical interfaces, appears in outline form; this is because it is surgically implanted in the sub-retinal space of the eye, i.e., between the retinal tissue and the choroid. Referring to FIG. 7B a schematic diagram of an embodiment of the electrode interface array 193's implant location is shown. In the embodiment, it is implanted in the area of the eye indicated in FIG. 7A, although it could be Implanted at several different locations on the eyeball to achieve the desired results. As depicted in FIG. 78 an incision in the sclera 199 of the eyeball is formed, creating a flap to insert the electrode interface array beneath. This flap exposes the target retinal tissue 197. Electrode Interface array 193 is placed in apposition to the retinal tissue 197. Because array 193 is built on a flexible substrate, it is able to bend to assume the curvature of the target location (the eyeball in this case), thus making good contact with the desired retina tissue all along the array. The sclera 199 is sutured closed over array 193, and the metal lead lines 191 run to metallic package 17, again as depicted in FIG. 7A. As depicted in FIGS. 7A and 7B electrode interface array 193 is a micro-matt like structure with an Iteration of many, perhaps hundreds, thousands or more of electrode interfaces 103 FIG. 4A, 107 FIGS. 6, 201, 203, 205 and 207 FIGS. 8 and 8A. It is micro-fabricated and highly flexible due to the flexible substrate. Each of the electrical interfaces would be electrically connected into the stimulation system disclosed herein.

Figure 8:
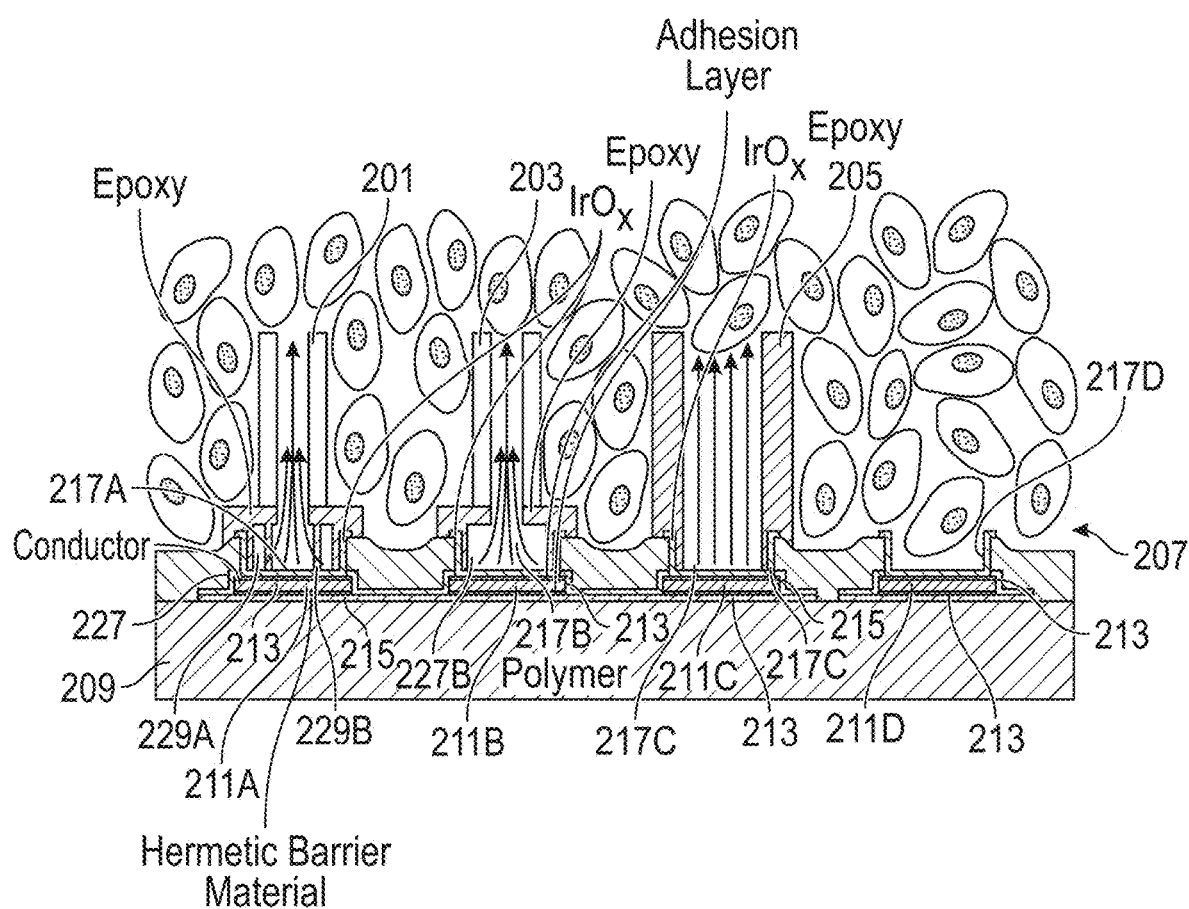
FIG. 8 is a schematic diagram with four different alternative embodiments of the electrode structure or interfaces of the present invention.

FIG. 8 provides cross-sectional views of additional embodiments 201, 203 and 205 of the electrode interface structures of the present invention which use a micro-fabricated hollow penetrating post or tube with an electrode positioned at its bottom. 207 is an example of an electrode with a substantially planar electrode surface. All four electrodes structures are fabricated on a flexible substrate 209 made of a polymer in the embodiment depicted. All four electrode structures sit on conductive lines 211A, 2118, 211C and 211D. These conductive lines in one embodiment can be metal conductive line and in the embodiment depicted they are made from evaporated gold having a thickness of from 100 nm to 10,000 nm depending on the application and are coated with a thin adhesive layer of Ti above and below.

Conductive lines 211A, B, C and D are further sealed by a hermetic barrier material 215, which in the embodiment depicted can be SiC, SiOC, a combination of SIC and SiOC, or any similar suitable material. Each conductive layer or path 211A, B, C, and D are electrically connected to respective conducting surfaces 217A, 6, C and D. The conductive surfaces, which are substantially planar in the cross-section depicted in FIG. 8 can be made from any suitable conducting material. In one embodiment they are made from a high charge injection material among which are the following possible materials that can be used: platinum, platinum black, titanium nitride, SIROF, anodic iridium oxide film (AIROF), electrodeposited iridium oxide film (EIROF), or thermal iridium oxide film (TIROF). The conductive surfaces 217A, B, C and D are encased in protective, flexible and insulating material 219. Typically, this material 219 is a suitable polymer which can be from 1 micron to 25 microns thick. Such suitable polymer that can be used for insulating layer 219 can include polyimide, silicone, polyurethane, parylene, polyethylene, polypropylene, peek, polyamide, polyester, PEEK, liquid crystal polymer, other polymers, or mixtures thereof.

Each interface structures 201, 203 and 205 include a tube or hollow post 221, 223 and 225. The hollow posts can be made from any suitable insulating material that holds it shape, yet will not produce significant foreign body reactions by the host or otherwise cause scarring. In the embodiment depicted, a suitable epoxy is used. Hollow post 221 sits on dome 215 over electrode surface 217A and hollow post 223 sits on dome 216 over electrode surface 2178.

Figure 8A:
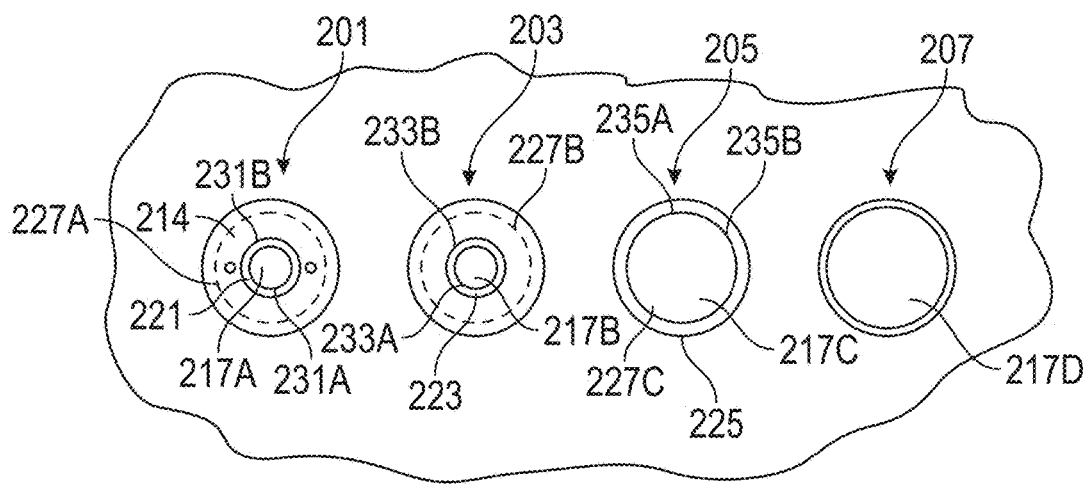
FIG. 8A is a top view of the electrode structures depicted in FIG. 8.

FIG. 8A is a top view of the interfacing structures depicted in FIG. 8. As depicted in FIGS. 8 and 8A each of the hollow posts 221 has an inner diameter 231A, and outer diameter 2318, hollow post 223 has an inner diameter of 233A and an outer diameter of 233B. Hollow post 225 has an inner diameter 235A and an outer diameter of 235B.

Referring to Figure BA as can be seen hollow posts 221 positioned over electrode surface 217A has a smaller inner diameter 231A than electrode surface 217A the edge of which is indicated by dotted line 227A. Also, dotted lines 229A and 2298. This corresponds to cross-sectional view in FIG. 8 where the edge 227 of electrode surface 271A can be seen and support posts 229A and 229B providing support for dome 214 are visible.

Hollow post 223 also has a smaller interior diameter 233A than the electrode surfaces 217B. This is visible in FIG. 8 where the edge 227B is visible. FIG. 8A also demonstrates this where the outside edge of electrode surface 217B is indicated by dotted line 227B. Dome 216 supports hollow post 223.

On the other had with electrode structure 205 its hollow post 225 has approximately the same inside diameter 235A as the outer diameter 227C of electrode surface 217C, referring to FIG. 8 and 8A. Likewise with electrode structure 207 electrode surface 217D is fully exposed referring to FIGS. 8 and 8A.

In some embodiments that actual surface area of each of the electrode surfaces 217A, B, C and D can vary from 100 square micrometers to 150,000 micrometers depending on the application that the electrode structure will be used for. The actual inner diameter 231A, 233A and 235A of each of the hollow posts can vary depending on the application. In some embodiments the inner diameter can vary from 5 micrometers to 50 micro meters. Outer diameter can vary from 7 micrometers to 100 micrometers. The height for the hollow posts in some applications can vary from 25 micrometers to 300 micrometers. The height of the dome over the electrode surface of hollow posts 221 and 223 can in some instances be from 1 micrometer to 50 micrometers. Spacing of the hollow posts with respect to each other in an array can vary from 15 micrometers to 500 micrometers center to center.

There may be some applications where one does not want the cells being stimulated to come in contact with the electrode surface, so hollow post with a diameter smaller than the target cell size would be used. This would allow interstitial fluid to enter the hollow post and make contact with the electrode surface and allow the creation of the desired electric field and resulting current flow, but prevent the cells from entering the hollow post as depicted with respect to hollow posts 221 and 223 in FIG. 8. Alternatively, one may limit cell growth in the hollow post to one or a few nerve cells as depicted with respect to electrode structures 205 and 207, and in those applications the interior diameter would be only so large to admit one or a few cells.

Even though one might want to prevent cells from coming in contact with the electrode surface directly one may need to still have a relatively large electrode surface to create the desired electric field or current flow, e.g. due to charge density limitations. In such instances interfaces 201 and 203 show their utility. With the dome structure depicted in FIGS. 8 and 8A, one can still present a large electrode surface using the dome structure depicted.

Figure 9:
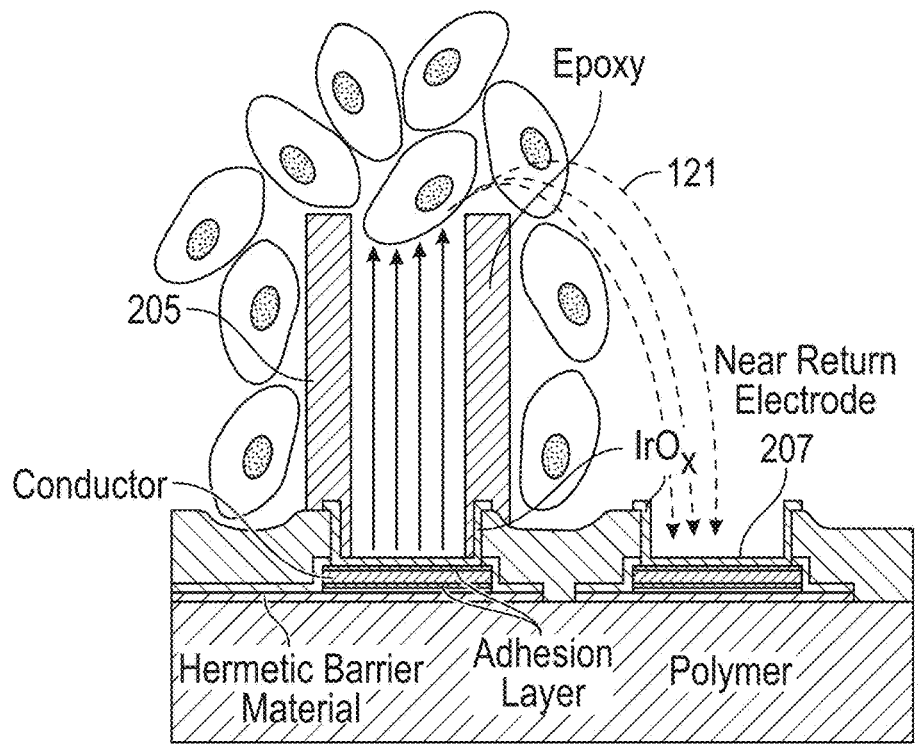
FIG. 9 is a schematic diagram of one of the alternative embodiments configures to generate a near electric field.
Figure 10:
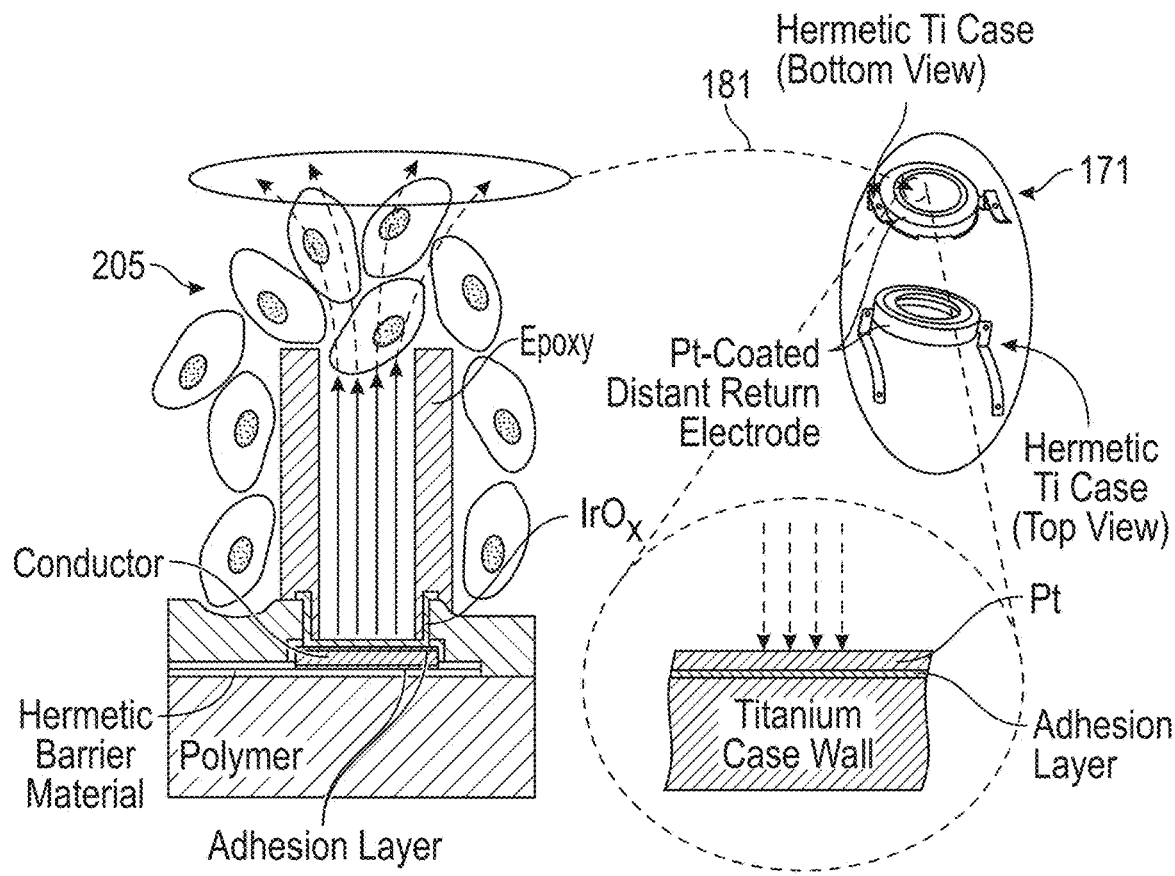
FIG. 10 is a schematic diagram of one of the alternative embodiments configures to generate a far electric field.

FIG. 9 depicts the embodiment of the electrode interface with a hollow post 205 positioned in a paired set up with electrode 207 to create a near electrical field. FIG. 10 depicts the embodiment of the electrode interface with a hollow post 205 positioned in a paired set up with electrode structure 171 to create a near electrical field An alternative option is to fill the hollow posts with a conductive solution or get. For example ionic content of the solution or get could be increased to improve conductivity. The solution could also include agents to inhibit ingress of cells, proteins, and/or other biological tissue. Alternatively, it could include agents to promote ingress of neurons or neuronal processes.

One possible method to fill the hollow posts with a desired material, get or liquid could entail evacuating the space created by the hollow post and chamber to less than 1 mTorr, covering the hollow tubes with the desired solution or get, and then slowly re-introducing an ambient pressure of from 760 Torr to 7,600 Torr to force the solution into the hollow posts and the electrode dome, if they are present.

The conductive mediums to fill the hollow posts to enhance focusing the electrical current or field could include isotonic saline solution or artificial interstitial fluid. The following could also be added: neurotrophic factors to promote neural growth, or alternatively, factors to inhibit neural growth.

The electrodes are normally pulsed with a bi-phasic current stimulus waveform consisting of a cathodic pulse and an anodic pulse, in order to maintain a net zero charge balance across the electrode tissue interface. The exact waveform shape for these current pulses can be optimized to obtain the lowest required signal strength to achieve the desired psychophysical result (e.g., perception, motion) in the subject.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. An interface for selectively making contact with a plurality of neural cells of a biological neural network comprising:
    a) a flexible substrate having a thickness of less than 0.1 mm with metal conductors encased in a highly bio-stable barrier layer further encased in one or more polymer protective layers;
    b) electrode surfaces made of high charge injection material electrically connected to said metal conductive layer;
    c) a tube, at a first end, surrounding each electrode surface, and said tube extending from said electrode surface to an open second end, said open second end providing exposure to neural tissue to said electrode surface;
    d) said tube being made of a conductive material covered by an electrically nonconductive material; and
    e) wherein said tube focuses an electrical field from the electrode surface during operation.

2. The interface of claim 1 where the interior opening and bore of at least one tube of said tube plurality of tubes is congruent with the outside edge of said electrode surface facing up said tube.

3. The interface of claim 1 wherein said interior opening and bore of at least one tube of said tube plurality of tubes has less surface area than that of said electrode surface and said first end of said at least one tube terminates at a dome covering said electrode surface.

4. An interface for selectively making electrical contact to a plurality of neural cells in a biological neural network, said interface comprising:
    a) a flexible substrate having a thickness of less than 0.1 mm and consisting of metal conductors encased in a highly bio-stable barrier layer further encased in one or more polymer protective layers; and
    b) a plurality of posts capable of carrying electrical current along their length, being partially or fully comprised of conducting material, which are electrically connected to said metal conductors; and said plurality of posts extends from said flexible substrate;

c) wherein said top surfaces of said posts are facing away from said substrate and can make electrical contact to said neural cells;

d) wherein said side surfaces of said posts are electrically isolated from surrounding neural tissue by an insulating layer, and are electrically isolated from each other; and e) wherein said metal conductors consist of evaporated Au having a thickness in the range of 100 nm to 10,000 nm, where the Au is coated above and below with a thin adhesion layer of Ti or completely wrapped in a thin adhesion layer of Ti.

5. The interface of claim 4 wherein said highly bio-stable barrier layer is selected from a group consisting of SiC, SiOC, a combination of SiC and SiOC, and a bilayer of SiC and SiOC.

6. The interface of claim 4 wherein said sides of said posts are electrically isolated by a polymer protective layer 1 micron to 25 microns thick, said polymer being selected from a group consisting of: polyimide, silicone, polyurethane, parylene, polyethylene, polypropylene, peek, polyamide, polyester, PEEK, liquid crystal polymer, Parylene-C, Parylene-D, Parylene-HT or Parylene-N, other polymers, and mixtures thereof.

7. The interface of claim 4 wherein said posts are 10 micrometers to 300 micrometers tall, are roughly cylindrical and 5 micrometers to 100 micrometers in diameter, and said posts are laterally spaced between 10 micrometers and 500 micrometers apart.

8. The interface of claim 7 wherein each of said plurality of posts extending from said flexible substrate have similar heights.

9. The interface of claim 7 wherein each of said plurality of posts extending from said flexible substrate have varying heights.

10. The interface of claim 4 wherein said posts are roughly cylindrical in shape with a top selected from a group consisting of: a flat top surface, a rounded top surface, and a pointed top surface.

11. An interface for selectively making electrical contact to a plurality of neural cells in a biological neural network, said interface comprising:

a) a flexible substrate having a thickness of less than 0.1 mm and consisting of metal conductors encased in a highly bio-stable barrier layer further encased in one or more polymer protective layers; and b) a plurality of posts capable of carrying electrical current along their length, being partially or fully comprised of conducting material, which are electrically connected to said metal conductors; and said plurality of posts extends from said flexible substrate;

c) wherein said top surfaces of said posts are facing away from said substrate and can make electrical contact to said neural cells;

d) wherein said side surfaces of said posts are electrically isolated from surrounding neural tissue by an insulating layer, and are electrically isolated from each other; and e) wherein said metal conductors consist of evaporated Au having a thickness in the range of 100 nm to 10,000 nm, where the Au is coated above with Pt having a thickness in the range of 10 nm to 1000 nm, where the Pt—Au bilayer is coated above and below with a thin adhesion layer of Ti or completely wrapped in a thin adhesion layer of Ti.

12. The interface of claim 11 wherein said highly bio-stable barrier layer is selected from a group consisting of SiC, SiOC, a combination of SiC and SiOC, and a bilayer of SiC and SiOC.

13. The interface of claim 11 wherein said sides of said posts are electrically isolated by a polymer protective layer 1 micron to 25 microns thick, said polymer being selected from a group consisting of: polyimide, silicone, polyurethane, parylene, polyethylene, polypropylene, peek, polyamide, polyester, PEEK, liquid crystal polymer, Parylene-C, Parylene-D, Parylene-HT or Parylene-N, other polymers, and mixtures thereof.

14. The interface of claim 11 wherein said posts are 10 micrometers to 300 micrometers tall, are roughly cylindrical and 5 micrometers to 100 micrometers in diameter, and said posts are laterally spaced between 10 micrometers and 500 micrometers apart.

15. The interface of claim 14 wherein each of said plurality of posts extending from said flexible substrate have similar heights.

16. The interface of claim 14 wherein said plurality of posts extending from said flexible substrate have varying heights.

17. An interface for selectively making electrical contact to a plurality of neural cells in a biological neural network, said interface comprising:

a) a flexible substrate having a thickness of less than 0.1 mm and consisting of metal conductors encased in a highly bio-stable barrier layer further encased in one or more polymer protective layers; and b) a plurality of posts capable of carrying electrical current along their length, being partially or fully comprised of conducting material, which are electrically connected to said metal conductors; and said plurality of posts extends from said flexible substrate;

c) wherein said top surfaces of said posts are facing away from said substrate and can make electrical contact to said neural cells;

d) wherein said side surfaces of said posts are electrically isolated from surrounding neural tissue by an insulating layer, and are electrically isolated from each other; and e) wherein said electrically conductive post comprises a superstructure of an electrically insulating material with an exposed electrically conductive layer at said top of said post, which electrically conductive layer extends down said side of said post between said superstructure and an electrically insulating layer to make electrical contact with said metal conductors.

18. The interface of claim 17 wherein said electrically conductive layer is high charge injection material and consists of at least one material selected from a group consisting of: platinum, platinum black, titanium nitride, puttered iridium oxide film (SIROF), anodic iridium oxide film (AIROF), electrodeposited iridium oxide film (EIROF), or thermal iridium oxide film (TIROF).

19. The interface according to claim 17 wherein said superstructure is formed from an electrically non-conductive structural material such as photoimageable epoxy.

20. The interface of claim 11 wherein said posts are roughly cylindrical in shape with a top selected from a group consisting of: a flat top surface, a rounded top surface, and a pointed top surface.

* * * * *

UNITED STATES PATENT AND TRADEMARK OFFICE
CERTIFICATE OF CORRECTION

| | |
|---|---|
| PATENT NO. | : 11,497,913 B1 |
| APPLICATION NO. | : 16/289519 |
| DATED | : November 15, 2022 |
| INVENTOR(S) | : Shire et al. |

It is certified that error appears in the above-identified patent and that said Letters Patent is hereby corrected as shown below:

In the Specification

Column 1, before Line 15, please insert the following paragraph:
--GOVERNMENT FUNDING
This invention was made with government support under EB022013, and EB018873 awarded by the National Institutes of Health. The government has certain rights in the invention.--

Signed and Sealed this
Second Day of May, 2023

*Katherine Kelly Vidal*

Katherine Kelly Vidal
*Director of the United States Patent and Trademark Office*